(12) United States Patent
Kang et al.

(10) Patent No.: US 10,584,312 B2
(45) Date of Patent: Mar. 10, 2020

(54) ISOLATING METHOD FOR UMBILICAL CORD BLOOD-DERIVED PLURIPOTENT STEM CELLS EXPRESSING ZNF281

(75) Inventors: Kyung Sun Kang, Seoul (KR); Kyoung Hwan Roh, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 0 days.

(21) Appl. No.: 13/257,961

(22) PCT Filed: Mar. 3, 2010

(86) PCT No.: PCT/KR2010/001338
§ 371 (c)(1),
(2), (4) Date: Sep. 20, 2011

(87) PCT Pub. No.: WO2010/107192
PCT Pub. Date: Sep. 23, 2010

(65) Prior Publication Data
US 2012/0021509 A1      Jan. 26, 2012

(30) Foreign Application Priority Data

Mar. 20, 2009   (KR) .................. 10-2009-0023821

(51) Int. Cl.
*C12N 5/0789*   (2010.01)
*A61K 35/12*    (2015.01)
(Continued)

(52) U.S. Cl.
CPC ......... *C12N 5/0605* (2013.01); *C12N 5/0647* (2013.01)

(58) Field of Classification Search
None
See application file for complete search history.

(56) References Cited

U.S. PATENT DOCUMENTS

2004/0009595 A1* 1/2004 Kremer et al. ............... 435/372
2004/0107453 A1* 6/2004 Furcht ................ A01K 67/0271
800/18
(Continued)

FOREIGN PATENT DOCUMENTS

JP    2004505627 A    2/2004
JP    2012520671 A   10/2012
(Continued)

OTHER PUBLICATIONS

Maurice et al. "Isolation of progenitor cells from cord blood using adhesion matrices." Cytotechnology 54:121-133 (2007).*
(Continued)

*Primary Examiner* — Blaine Lankford
*Assistant Examiner* — Lauren K Van Buren
(74) *Attorney, Agent, or Firm* — Cooley LLP

(57) ABSTRACT

The present invention relates to a method for isolating pluripotent/multipotent stem cells derived from umbilical cord blood, characterized by culturing mononuclear cells isolated from umbilical cord blood in a culture vessel containing fibronectin and then harvesting stem cells from the culture, the umbilical cord blood-derived pluripotent/multipotent stem cells isolated thereby; and a cell therapeutic agent containing the pluripotent/multipotent stem cells derived from umbilical cord blood or cells differentiated therefrom. The present invention also relates to a novel culture media for stem cells, a culture method for stem cells which is characterized by culturing and proliferating stem cells in the culture media, and a method for increasing sternness of stem cells which is characterized by a sphere culture or a three-dimensional culture of stem cells.

8 Claims, 12 Drawing Sheets

Specification includes a Sequence Listing.

(51) Int. Cl.
A61K 35/44 (2015.01)
C12N 5/073 (2010.01)

(56) References Cited

U.S. PATENT DOCUMENTS

| | | | |
|---|---|---|---|
| 2006/0183103 A1* | 8/2006 | Wagner et al. | 435/2 |
| 2006/0223177 A1* | 10/2006 | Harris | C12N 5/0607 435/325 |
| 2009/0047257 A1* | 2/2009 | Laughlin | C12N 5/0692 424/93.7 |

FOREIGN PATENT DOCUMENTS

| | | | |
|---|---|---|---|
| WO | WO 2005/056778 A1 | | 6/2005 |
| WO | WO2007064090 | * | 6/2007 |
| WO | WO 2008/110570 A1 | | 9/2008 |
| WO | WO 2008/149129 A1 | | 12/2008 |

OTHER PUBLICATIONS

Kassis et al. "Isolation of mesenchymal stem cells from G-CSF-mobilized human peripheral blood using fibrin microbeads" Bone Marrow Transplantation (2006) 37, 967-976.*
Liu et al. "Differential gene expression in human hematopoietic stem cells specified toward erythroid, megakaryocytic, and granulocytic lineage." Journal of Leukocyte Biology, vol. 82, Oct. 2007, 986-1002.*
Javed et al. "Endothelial Colony Forming Cells and Mesenchymal Stem Cells are Enriched at Different Gestational Ages in Human Umbilical Cord Blood" Pediatric Research 64(1): 68-73, 2008.*
Pilling et al. "Identification of Markers that Distinguish Monocyte-Derived Fibrocytes from Monocytes, Macrophages, and Fibroblasts." Plus One, Oct. 2009, vol. 4, Issue 10.*
Sohlberg et al. "Cord blood monocyte subsets are similar to adult and show potent peptidoglycan-Stimulated cytokine response." Immunology, 133, 41-50.*
Maurice et al. "Isolation of progenitor cells from cord blood using adhesion matrices" Cytotechnology (2006) 52: 125-137.*
Martin et al. "Stimulation of Human Monocyte/Macrophages Derived Growth Factor (MDGF) Production by Plasma Fibronectin." Am J. of Pathology, v. 111 (3): Jun. 1983.*
Nagano et al. "Identification of functional endothelial progenitor cells suitable for the treatment of ischemic tissue using human umbilical cord blood." Blood 2007, 110: 151-160.*
Martin et al. "Simulation of Human Monocyte/Macrophage Derived Growth Factor (MDGF) Produced by Plasma Fibronectin." Am J. Pathology v. 111(3): Jun. 1983.*
Suga et al. "Rapid expansion of human adipose-derived stromal cells preserving multipotency" Cytotherapy (2007) vol. 9, No. 8, 738-745.*
Nagano et al. "Identification of functional endothelial progenitor cells suitable for the treatment of ischemic tissue using human umbilical cord blood." Blood 2007, 110: 151-160. (Year: 2007).*
Martin et al. "Simulation of Human Monocyte/Macrophage Derived Growth Factor (MDGF) Produced by Plasma Fibronectin." Am J. Pathology v. 111(3): Jun. 1983. (Year: 1983).*
Suga et al. "Rapid expansion of human adipose-derived stromal cells preserving multipotency" Cytotherapy (2007) vol. 9, No. 8, 738-745. (Year: 2007).*
Bhakta, et al., "Umbilical Cord Blood Stem Cells for Myocardial Regeneration and Angiogenesis", Comtemporary Cardiology Stems and myocardial Regeneration, edited by M.S. Penn, 2007, pp. 67-81.
Kogler, et al., "Comparative generation and characterization of pluripotent unrestricted somatic stem cells with mesenchymal stem cells from human cord blood", Experimental Hematology, 2006, vol. 34, pp. 1589-1595.
Kim, et al., "An Extended Transcriptional Network for Pluripotency of Embryonic Stem Cells", Cell, 2008, vol. 132, pp. 1049-1061.
Maurice, et al., "Isolation of progenitor cells from cord blood using adhesion matrices", Cytotechnology, 2007, vol. 54, pp. 121-133.
International Search Report dated Jan. 5, 2011 of International Patent Application No. PCT/KR2010/001338, filed Mar. 3, 2010.
M. Jawad Javed et al., "Endothelial Colony Forming Cells and Mesenchymal Stem Cells are Enriched at Different Gestational Ages in Human Umbilical Cord Blood," Pediatric Research 64(1): 68-73, 2008.
Seon-Kyung Lee et al., "ZNF281 Regulates the Stemness of Human Umbilical Cord Blood Derived Mesenchymal Stem Cell (huCB-MSC)," Korean Society for Zoonoses, Inaugural Assembly and Symposium Book of Abstracts, 2008, vol. 1, p. 392.
Sun, W. et al., "Voltage-Sensitve and ligand-Gated Channels in Differentiating Neural Stem-Like Cells Derived from the Nonhematopoietic Fraction of Human Umbilical Cord Blood," Stem Cells, 23:931-945, 2005.
Hong, et al., "In vitro differentiation of human umbilical cord blood-derived mesenchymal stem cells into hepatocyte-like cells," Biochem. Biophys. Res. Commun., 30:1153-1161, 2005.
Hutson, et al., "Rapid Isolation, Expansion, and Differentiation of Osteoprogenitors from Full-Term Umbilical Cord Blood," Tissue Engineering, 11:1407-1420, 2005.
Nonome, et al., "Human umbilical cord blood-derived cells differentiate into hepatocyte-like cells in the Fas-mediated liver injury model," Am, J. Physiol. Gastrointest. Liver Physiol., 289:1091-1099, 2005.
Yoshida, et al., "Human Cord Blood-Derived Cells Generate Insulin-Producing Cells in Vivo", Stem Cells, 23: 1409-1416, 2005.
Kim, et al., "Cell Transplantation Improves Ventricular Function After a Myocardial Infarction: A Preclinical Study of Human Unrestricted Somatic Stem Cells in a Porcine Model," Circulation, 112:96-104, 2005.
Claudio, et al., "Umbilical Cord Blood Transplantation and Banking," Annual Review of Medicine, 57:403-417, 2006.
Grewal, et al., "Successful hempatopoietic stem cell transplantation for Fanconi anemia from an unaffected HLA-genotype-identical sibling selected using preimplantation genetic diagnosis," Blood, 103:1147-1151, 2004.
Knutsen, et al., "Umbilical cord blood transplantation in Wiskott Aldrich syndrome," Journal pediatrics, 142:519, 2003.
Ooi, et al., "Unrelated cord blood transplantation for adult patients with de novo acute myeloid leukemia," Blood, 103:489-491, 2004.
Kim, et al., "Successful Stem Cell Therapy Using Umbilical Cord Blood-Derived Multipotent Stem Cells for Buerger's Disease and Ischemic Limb Disease Animal Model," 42:1620-1626Stem Cells, 2006.
Kang et al., "A 37-year-old spinal cord-injured female patient, transplanted of multipotent stem cells from human UC blood, with improved sensory perception and mobility, both functionally and morphologically: a case study," Cytotherapy, 7:368-373, 2005.
Fukuoka, et al., "Cloning and characterization of the guinea pig C5a anaphylatoxin receptor: interspecies diversity among the C5a receptors," International Immunology, 10(3):275-283, 1998.
Simmons, et al., "Isolation of a cDNA Encoding cd33, a differentiation antigen of myeloid progenitor cells," Journal of Immunology, 141(8):2797-2800, 1998.
Cristofalo et al., "Relationship between donor age and the replicative lifespan of human cells in culture: A reevaluation," Proc. Natl. Acad. Sci., USA 95, pp. 10614-10619, 1998.
Wang, et al., "A protein interaction network for pluripotency of embryonic stem cells," Nature, vol. 444, pp. 364-368, Nov. 16, 2006.
Law, et al., "ZBP-99 Defines a Conserved Family of Transcription Factors and Regulates Omithine Decarboxylase Gene Expression," Biochemical and Biophysical Research Communications 262, 113-120 (1999).
Lisowsky, et al., "Identification of human GC-box-binding zinc finger protein, a new Kruppel-like zinc finger protein, by the yeast one-hybrid screening with a GC-rich target sequence," FEBS Lett 453, (1999) 369-374.
Koch, et al. "Large-Scale Identification of c-MYC-Associated Proteins using a Combined TAP/MudPIT Approach," Cell Cycle 6, 205-217 (2007).

(56) References Cited

OTHER PUBLICATIONS

Tai, et al., "Oct4 expression in adult human stem cells: evidence in support of the stem cell theory of carcinogenesis," Carcinogenesis, vol. 26, No. 2, pp. 495-502, 2005.

Tondreau, et al., "Mesenchymal Stem Cells Derived from CD133-Positive Cells in Mobilized Peripheral Blood and Cord Blood: Proliferation, Oct4 Expression, and Plasticity," Stem Cells, 23:1105, 2005.

Takahashi, et al., Induction of Pluripotent Stem Cells from Adult Human Fibroblasts by Defined Factors,: Cell, 131 (5), 861-872, 2007.

Avram, et al., "Subcutaneous fat in normal and diseased states," J. Am Acad Dermatol, 56(3), 472-492, 2007.

Cho, et al., "Induction of osteogenic differentiation of human mesenchymal stem cells by histone deacetylase inhibitors," Journal of Cellular Biochemistry, 96, 533-542, 2005.

Kim et al., "An Extended Transcriptional Network for Pluripotency of Embryonic Stem Cells," Cell 132: 1049-1061, Mar. 21, 2008.

Lee et al., "ZNF281 Regulates the Stemness of Human Umbilical Cord Blood derived Mesenchymal Stem Cell *hUCB-MSC)," Abstract No. P-95, p. 392, Dec. 31, 2008.

Sun Yan, "Inducing Differentiation of Human Umbilical Cord Blood Stem Cells into Hepatocyte-like Cells in Vitro," Postgraduate, The Institute of Digestive Disease, Zhenqzhou University, Zhengzhou, 450052, six pages, 2004.

Seo et al., "ZNF281 Knockdown Induced Osteogenic Differentiation of Human Multipotent Stem Cells In Vivo and In Vitro," Cell Transplantation 22: 29-40, 2013.

Kögler et al., "A new Human Somatic Stem Cell from Placental Cord Blood with Intrinsic Pluripotent Differentiation Potential," J. Exp. Med., 200(2):123-135, Jul. 19, 2004.

Wang et al., "The Transcription Factor Zfp281 Controls Embryonic Stem Cell Pluripotency by Direct Activation and Repression of Target Genes," Stems Cells 26:2791-2799, 2008.

Zhao et al., "Identification of stem cells from human umbilical cord blood with embryonic and hematopoietic characteristics," Experimental Cell Research 312:2454-2464, 2006.

\* cited by examiner

[Fig. 1]
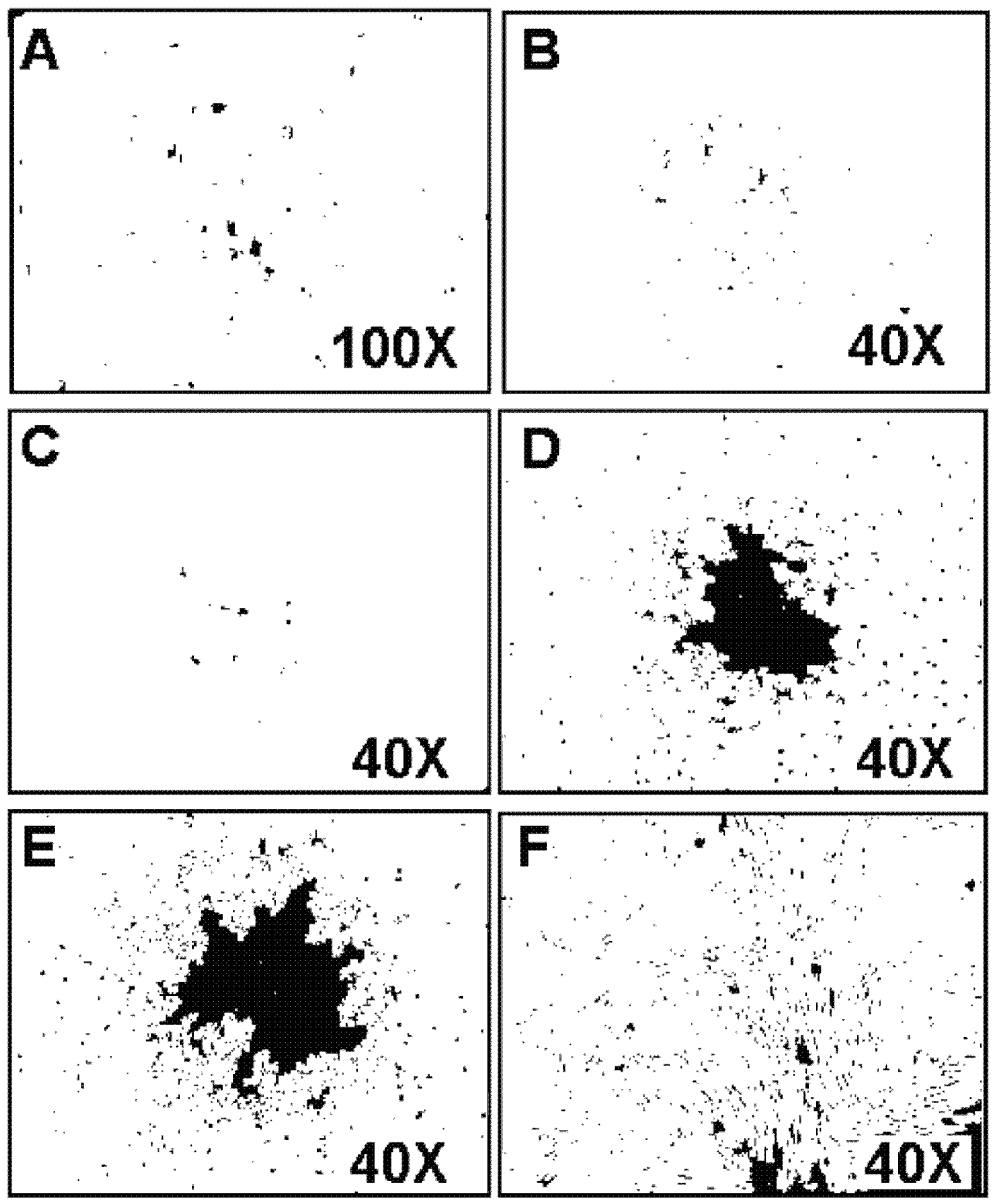

[Fig. 2]
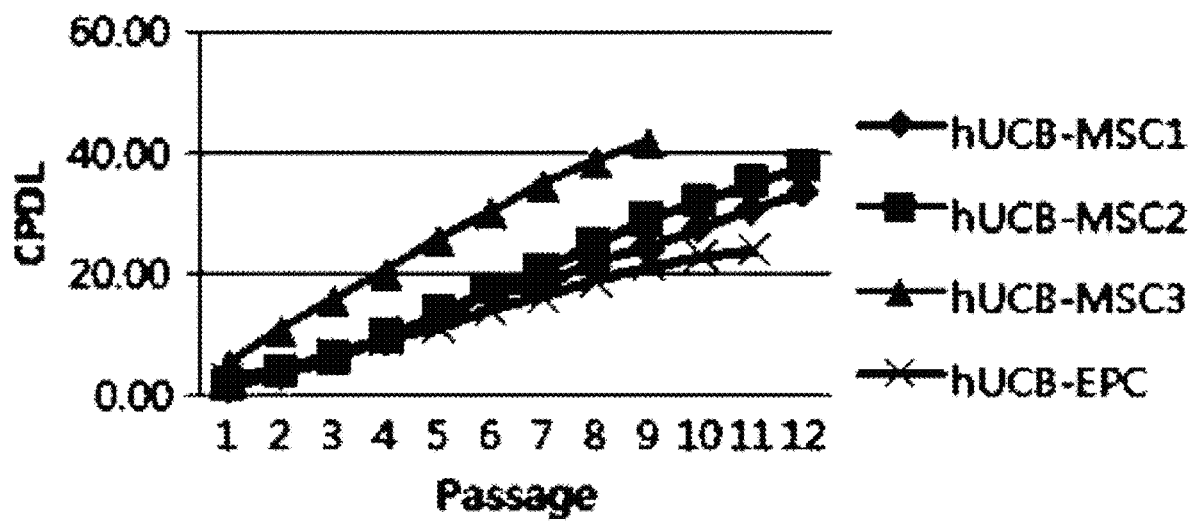
[Fig. 3]
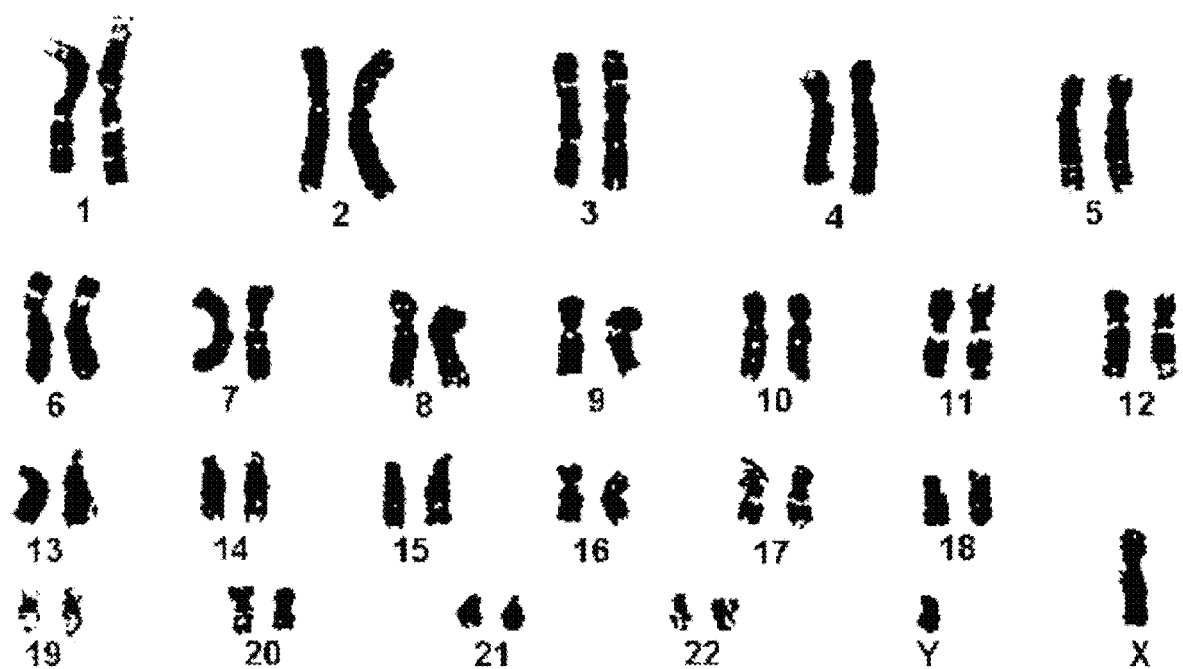

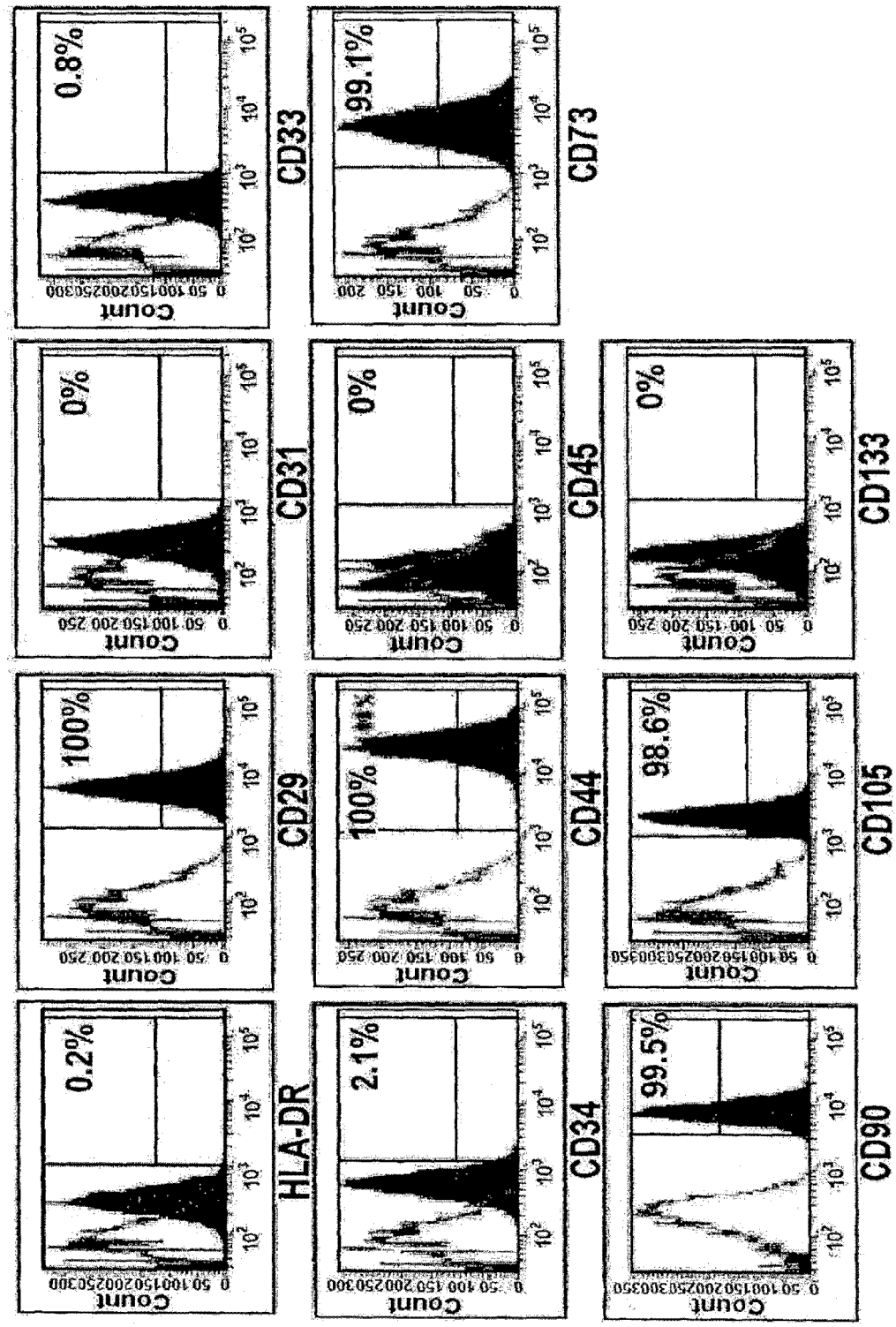
[Fig. 4]

[Fig. 5]
A
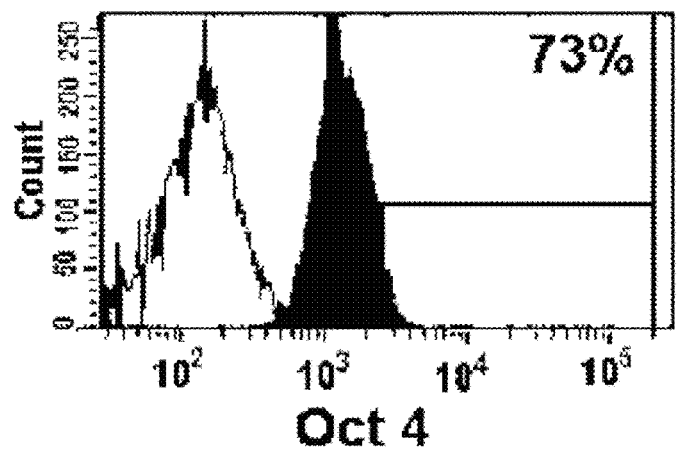
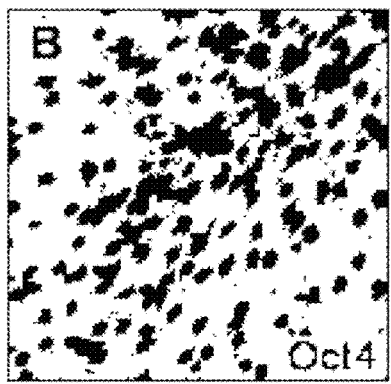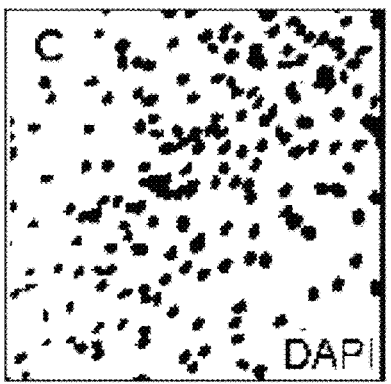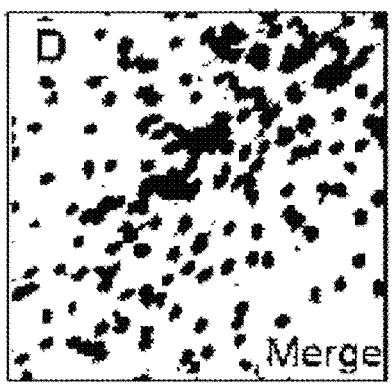

[Fig. 6]
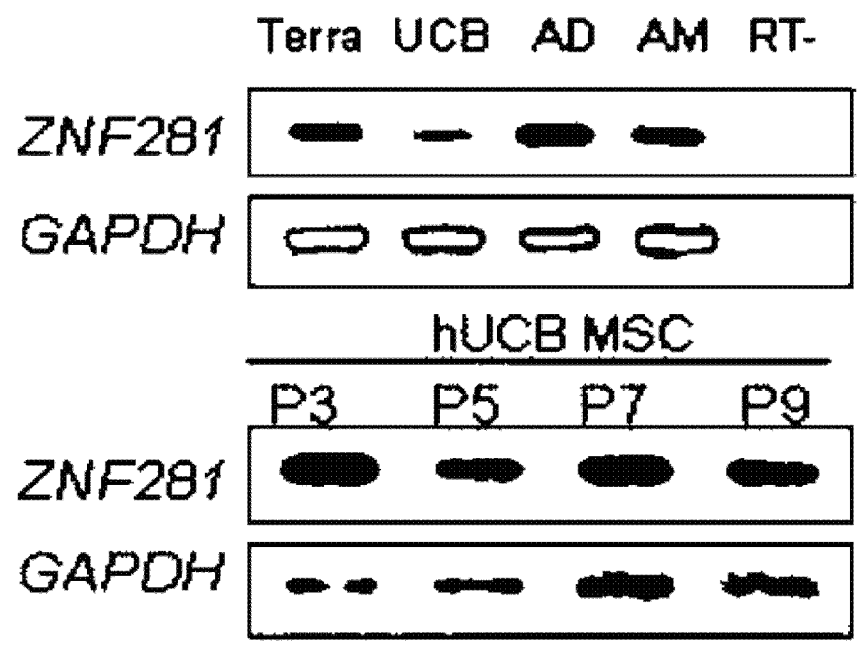
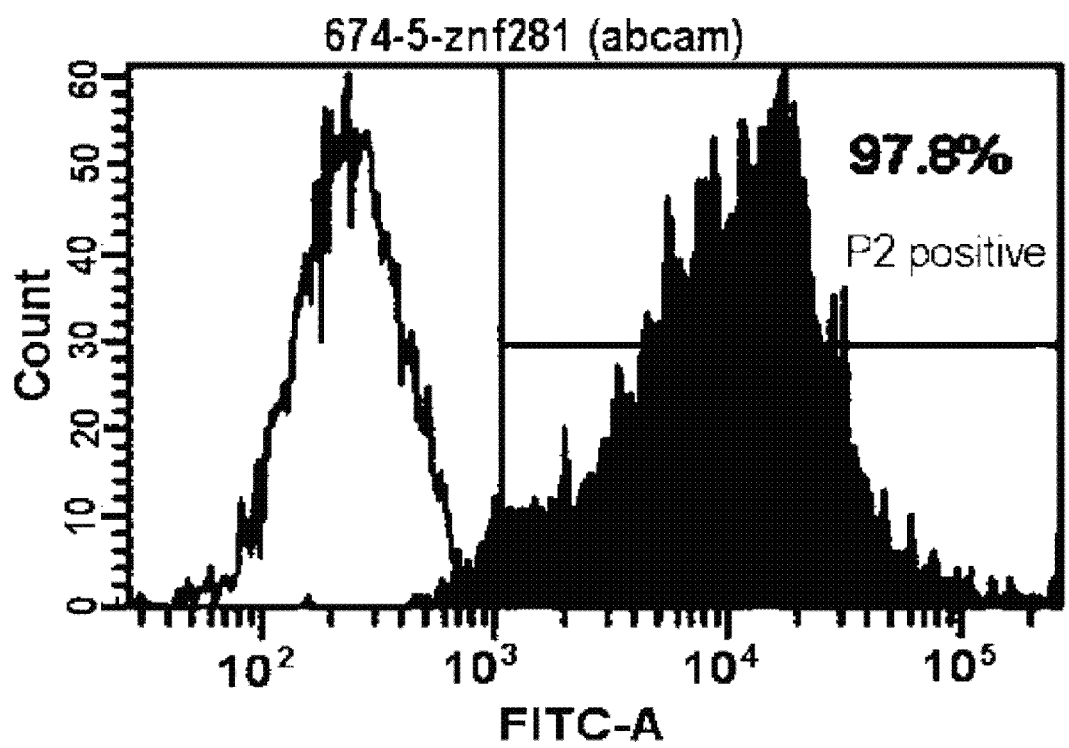

[Fig. 7]
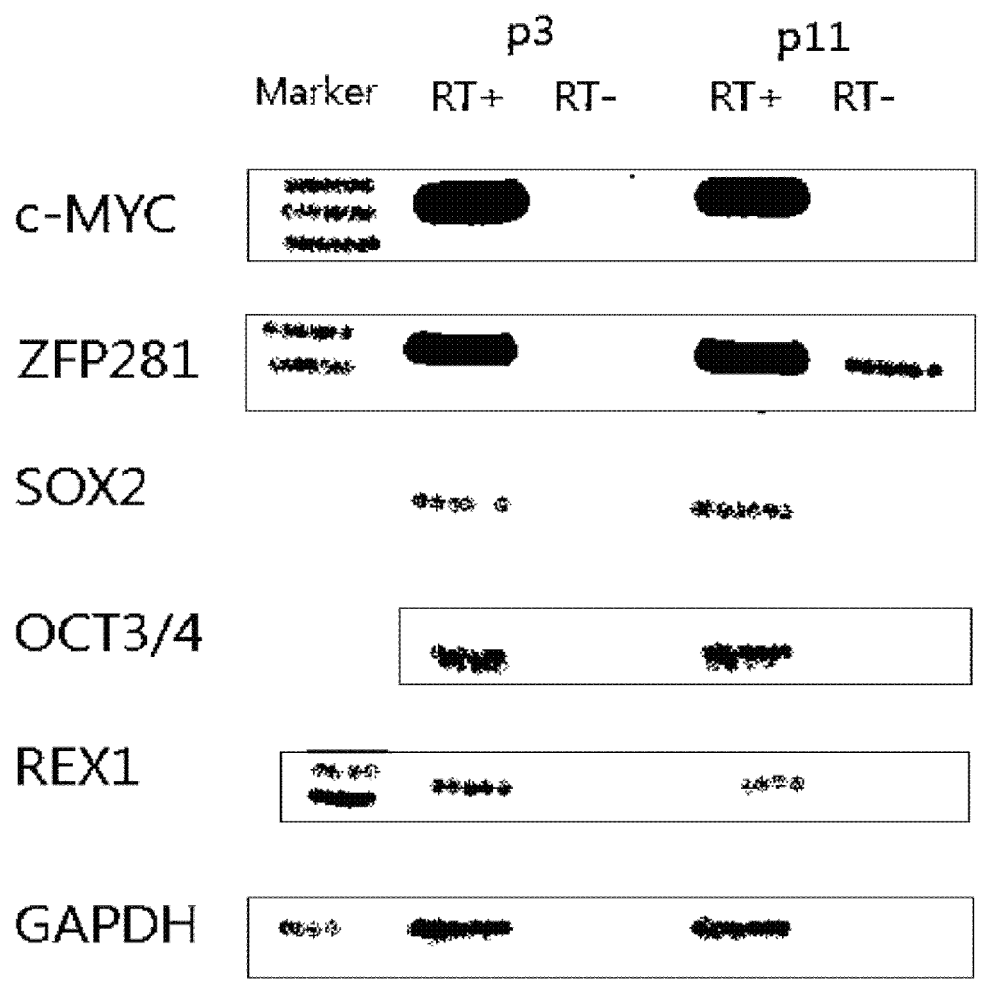

[Fig. 8]
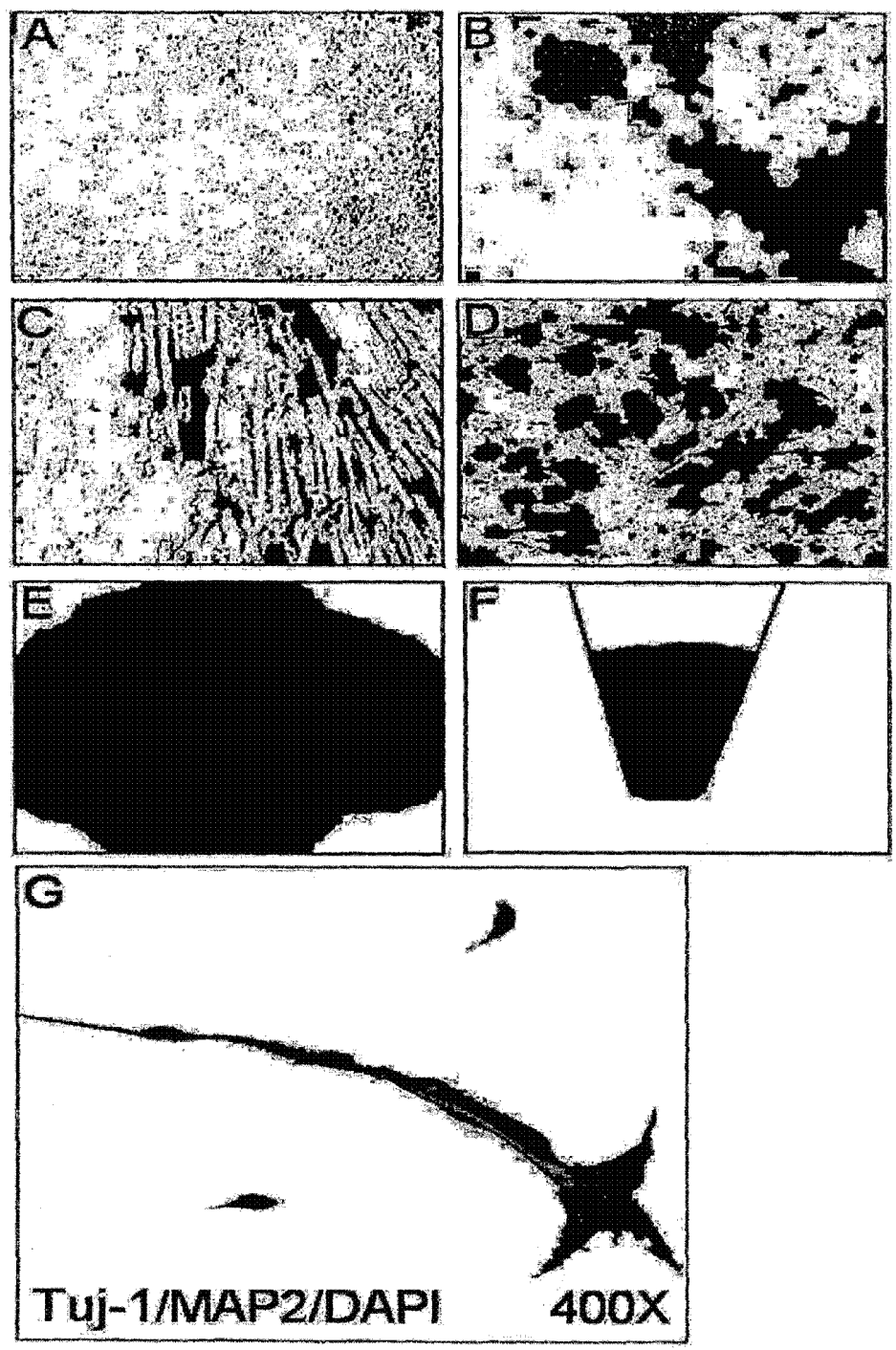

[Fig. 9]
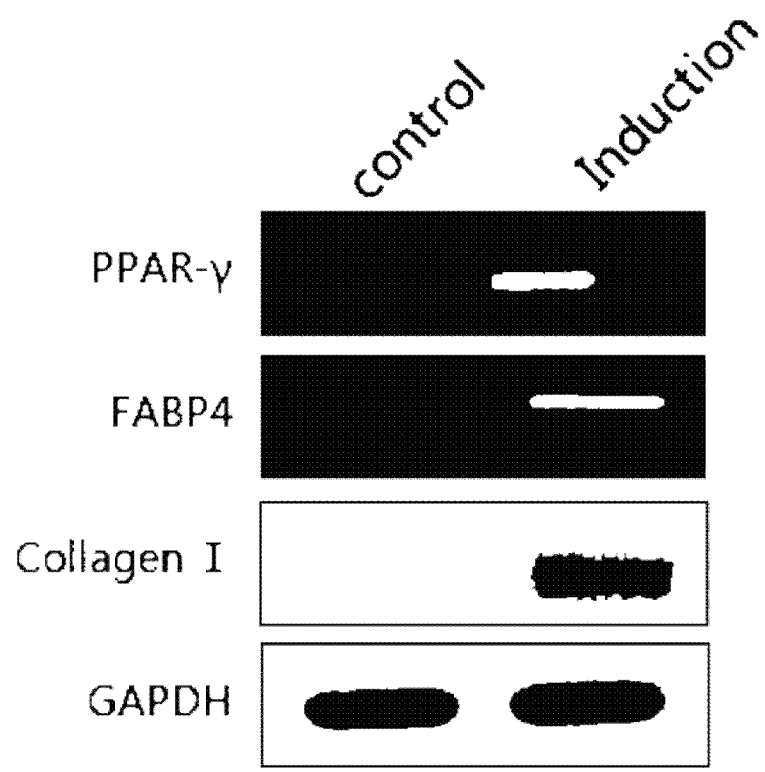

[Fig. 10]
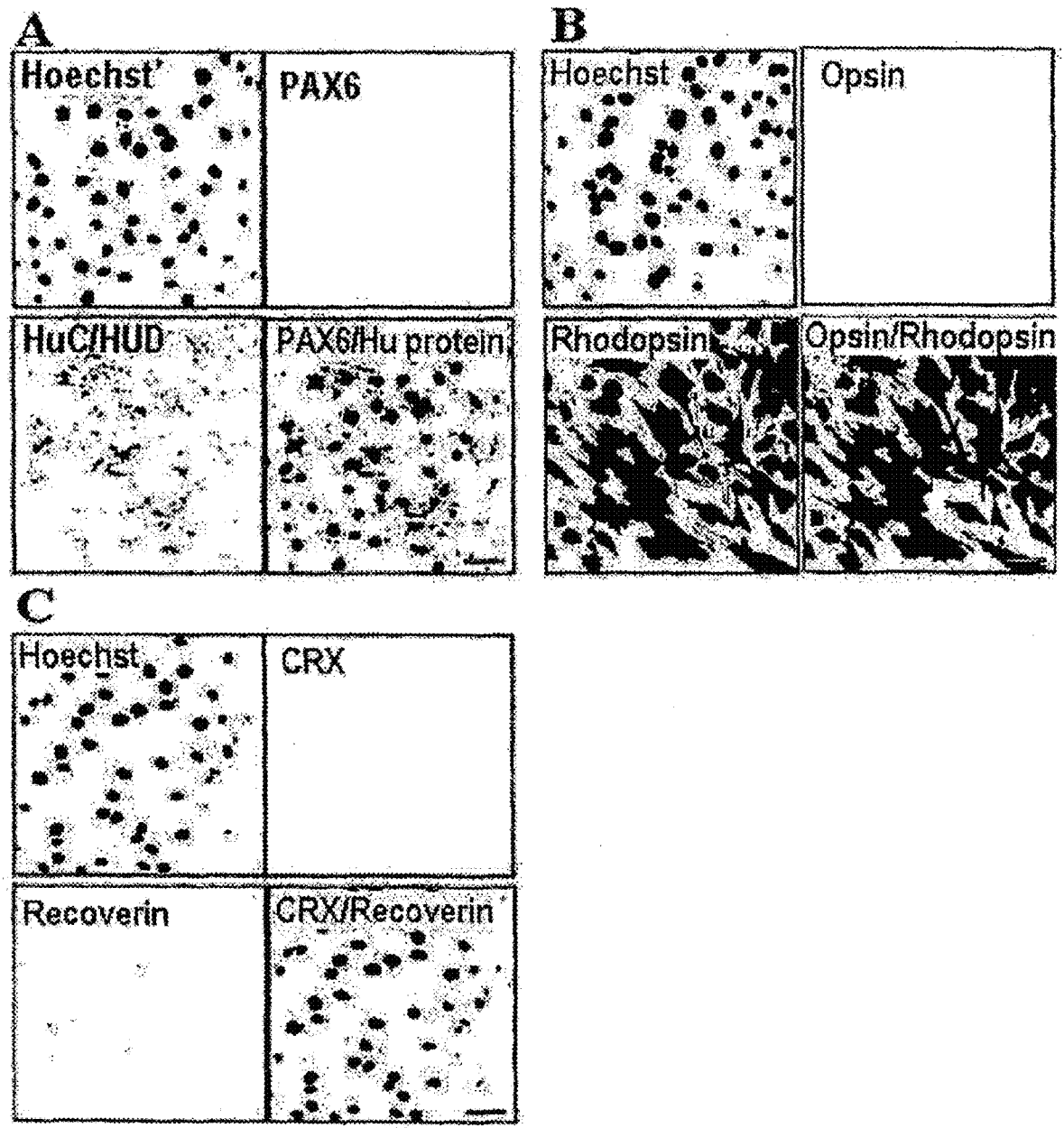

[Fig. 11]

[Fig. 12]
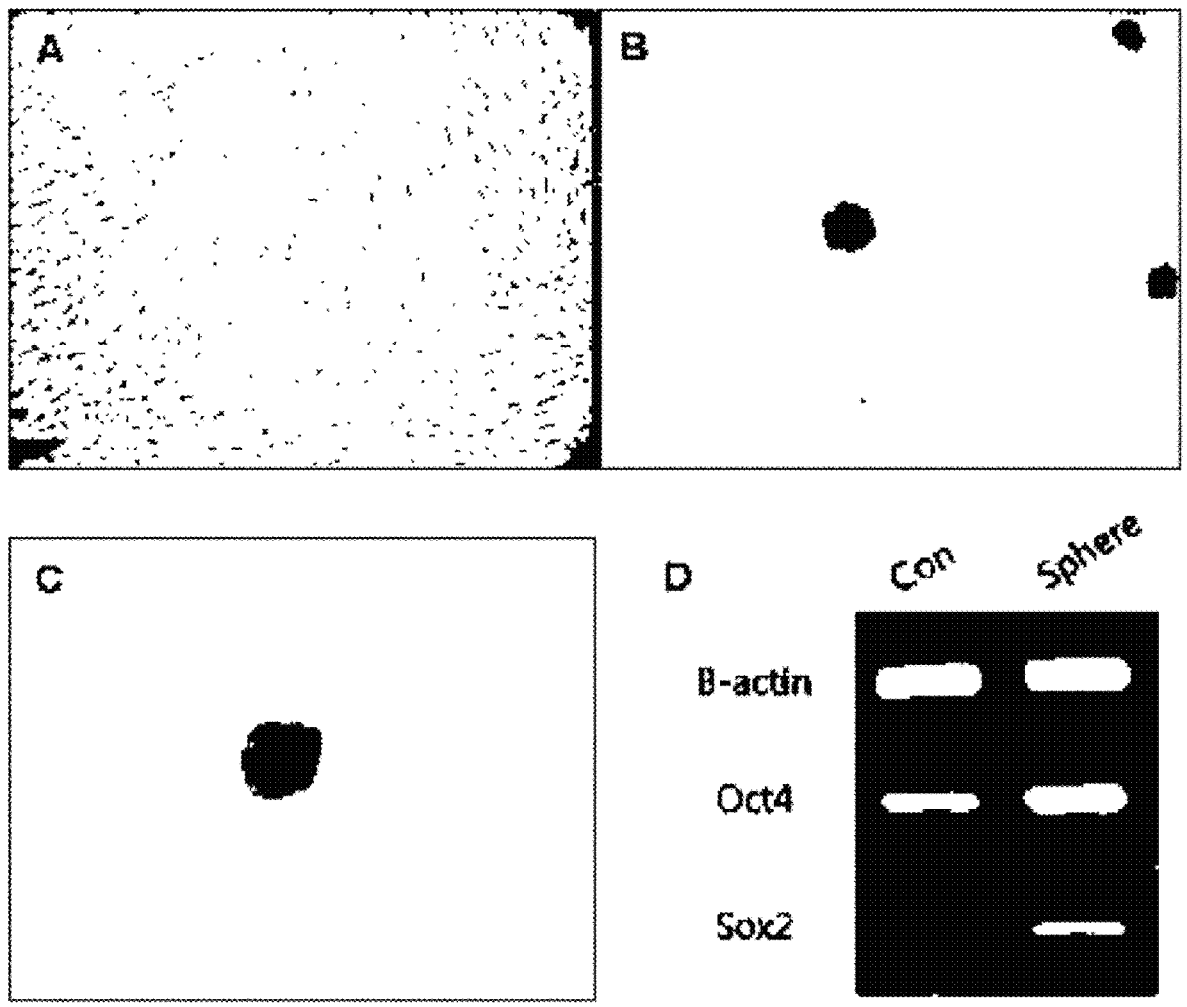

[Fig. 13]
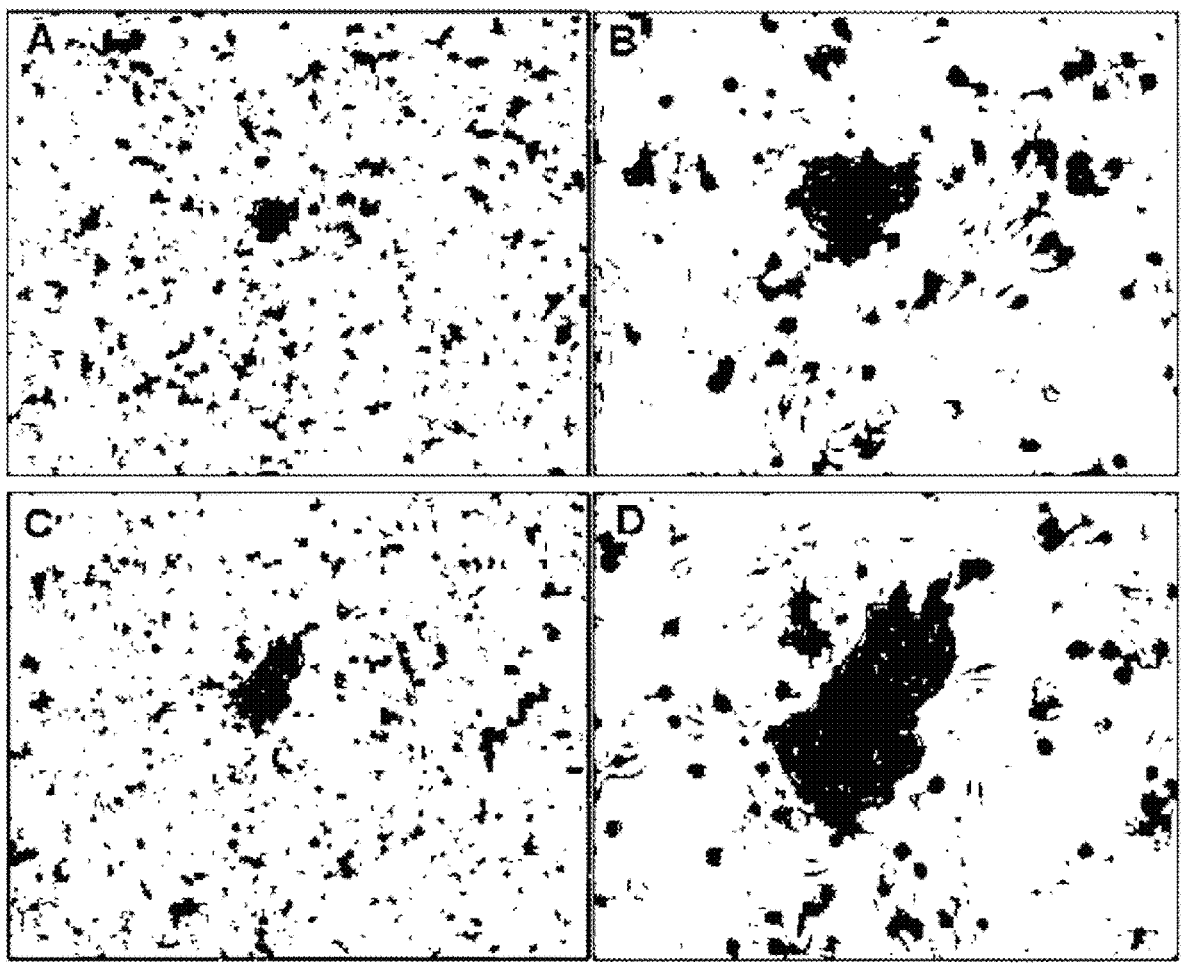

ISOLATING METHOD FOR UMBILICAL CORD BLOOD-DERIVED PLURIPOTENT STEM CELLS EXPRESSING ZNF281

CROSS-REFERENCE TO RELATED APPLICATIONS

This application is a U.S. national phase application of International PCT Patent Application No. PCT/KR2010/001338, which was filed on Mar. 3, 2010, which claims priority to Korean Patent Application No. 10-2009-0023821, filed Mar. 20, 2009. These applications are incorporated herein by reference in their entireties.

TECHNICAL FIELD

The present invention relates to a method for isolating pluripotent/multipotent stem cells derived from umbilical cord blood, characterized by culturing mononuclear cells isolated from umbilical cord blood in a culture vessel containing fibronectin and then harvesting stem cells from the culture, the umbilical cord blood-derived pluripotent/multipotent stem cells isolated thereby; and a cell therapeutic agent containing the pluripotent/multipotent stem cells derived from umbilical cord blood or cells differentiated therefrom. The present invention also relates to a novel culture media for stem cells, a culture method for stem cells which is characterized by culturing and proliferating stem cells in the culture media, and a method for increasing sternness of stem cells which is characterized by a sphere culture or a three-dimensional culture of stem cells.

BACKGROUND ART

Characterized by being self-renewing, undergoing differentiation and being immortal, stem cells have been proposed to be a solution for the problems of regenerative medicine and tissue replacement so that they can be used to treat various degenerative diseases as well as to provide deep insight into cellular biology. Adult stem cells, obtainable from various tissues, are far more attractive than embryonic stem cells because of the ability to come from an unlimited number of sources and the ethical objections to using human embryos as a source of cells are rendered irrelevant. Moreover, stem cells isolated from umbilical cord blood have advantages over other adult stem cells in that the donors of umbilical cord blood are not injured, unlike the donors of bone marrow or adipose tissue.

Umbilical cord blood-derived mesenchymal stem cells have been successfully introduced into various kinds of cells including neural cells, hepatocytes, osteocytes, etc., in vitro (Sun, W. et al., Stem cells, 23:931, 2005; Hong S H. et al., Biochem. Biophys. Res. Commun., 30:1153, 2005; Hutson E L. et al., Tissue Engineering, 11:1407, 2005). Successful in vivo transplantation of umbilical cord blood-derived mesenchymal stem cells for injuries, diabetes mellitus and heart infarction were also reported (Nonome, K. et al., Am, J. Physiol. Gastrointest. Liver Physiol., 289:1091, 2005; Yoshida, S. et al., Stem cells, 23:1409, 2005; Kim Bo. et al., Circulation, 112:96, 2005). Due to the low possibility of infectious diseases being transmitted and the low possibility of causing graft-versus-host diseases, the transplantation of umbilical cord blood-derived mesenchymal stem cells has been increasingly applied to both child and adult patients (Claudio G. B. et al., Annual Review of Medicine, 57:403, 2006). Although umbilical cord blood transplantation has been accepted as a therapy for some diseases, particularly hematopoietic defection-related diseases (Grewal, S S. et al., Blood, 103:1147, 2004; Knutsen, A P. et al., Journal pediatrics, 142:519, 2003; Ooi, J. et al., Blood, 103:489, 2004; Sanz G F. et al., Blood, 103:489, 2004), studies on the clinical application of umbilical cord blood-derived mesenchymal stem cells are still limited. For example, there are reports on stem cells being used to successfully cure, not completely but partially, women having spinal cord injuries and patients with Buerger's disease (Kim, S W. et al., Stem Cells, 2006; Kang, K S. et al., Cytotherapy, 7:368, 2005). However, the mechanism of development of the cells or how to grow and proliferate them still remains unknown.

It is difficult to isolate mesenchymal stem cells from umbilical cord blood. For example, when the method used to isolate bone marrow-derived mesenchymal stem cells is applied to umbilical cord blood, the isolation rate remains at around 20%. As much as 50% of the mesenchymal stem cells may be isolated from flesh blood which has been taken 5 hours before the isolation. However, the isolation rate is decreased to 20% or less when the blood has been taken over 5 hours before doing the isolation and the cells, although isolated, do not proliferate well.

DISCLOSURE

Technical Problem

Leading to the present invention, intensive and thorough research into the isolation and mass proliferation of stem cells from umbilical cord blood, conducted by the present inventors, resulted in the finding that when cultured in the presence of fibronectin, mononuclear cells isolated from human umbilical cord blood highly proliferate and form colonies, exhibiting a spindle shaped morphology, and maintain stem cell properties even after many passages. Therefore, based on the finding, a method is provided for effectively isolating umbilical cord blood-derived non-hematopoietic pluripotent/multipotent stem cells and mesenchymal stem cells and for proliferating them on a mass scale.

It is therefore an object of the present invention to provide a method for isolating umbilical cord blood-derived pluripotent/multipotent stem cells, comprising culturing mononuclear cells isolated from umbilical cord blood in the presence of fibronectin and recovering stem cells from the culture.

It is another object of the present invention to provide umbilical cord blood-derived pluripotent/multipotent stem cells isolated by the isolation method.

It is a further object of the present invention to provide a cell therapeutic agent comprising the umbilical cord blood-derived pluripotent/multipotent stem cells or cells differentiated therefrom.

It is still a further object of the present invention to provide a novel culture medium for stem cells.

It is still another object of the present invention to provide a method for culturing stem cells, using the culture medium.

It is a method for increasing sternness of stem cells, using a sphere culture or three-dimensional culture of stem cells.

Technical Solution

In accordance with an aspect thereof, the present invention pertains to a method for isolating umbilical cord blood-derived stem cells, characterized by culturing mononuclear cells isolated from umbilical cord blood in a culture vessel containing fibronectin and harvesting the stem cells from the culture.

In one embodiment, the step of harvesting the stem cells from the culture comprises utilizing an immunological property of stem cells to separate the stem cells.

The isolation of mononuclear cells from umbilical cord blood may be achieved using a typical method. After mixing the umbilical cord blood with Hetasep to deplete erythrocytes, mononuclear cells are isolated using Ficoll-paque. Herein, Hetasep is preferably used in an amount of 0.5~2 mL per 5 mL of Hetasep.

To increase the isolation yield of mononuclear cells therefrom, the umbilical cord blood used in the present invention is preferably one that is recovered immediately after childbirth, one that is stored at room temperature for 12~48 hours after the recovery, or one that is stored at 3~5° C. for 6~72 hours after the recovery.

The isolation of stem cells from the umbilical cord blood-derived mononuclear cells is characterized by the use of fibronectin. The term "culture vessel containing fibronectin," as used herein, is intended to mean a condition in which mononuclear cells can be brought into contact with fibronectin. For example, fibronectin may be layered on a culture vessel or may be contained in the form of spheres or three-dimensional structures in a culture medium. In one embodiment of the present invention, when the culture vessel is coated therewith, fibronectin may be contained at a density of from 0.1 to 1 mg/mL.

The fibronectin useful in the present invention may be derived from animals without limitation and preferably from humans. Also, the fibronectin may be prepared by artificial synthesis (e.g., chemical synthesis, synthesis using a peptide synthesizer, etc.) or biosynthesis (e.g., recombinant DNA technology, fibroblast culture, etc.) or may be separated from the plasma of animals including humans from the extracellular matrices. The fibronectin may be a fragment or peptide sequence of fibronectin or may contain the fragment or peptide.

No particular limitations are imparted to the medium available when the mononuclear cells are cultured in the culture vessel containing fibronectin. SNU-1 or EGM-2 is preferably used as a fundamental medium for culturing the mononuclear cells.

The SNU-1 medium contains the following composition (Table 1).

TABLE 1

| | SNU-1 (mg/l) | | SNU-1 (mg/l) | | SNU-1 (mg/l) |
|---|---|---|---|---|---|
| $CaCl_2$ (anhyd.) | 200 | L-Isoleucine | 78 | i-Inositol | 3 |
| KCL | 400 | L-Leucine | 78 | Riboflavin | 0.15 |
| $MgSO_4$ (anhyd.) | 97.67 | L-Lysine HCl | 108.75 | Thiamine HCl | 1.5 |
| NaCl | 7635 | L-Methionine | 22.5 | L-Alanine | 17.8 |
| $NaH_2PO_4H_2O$ | 140 | L-Phenyl-alanine | 48 | L-Asparagine $H_2O$ | 30 |
| D-Glucose | 1000 | L-Serine | 21 | L-Aspartic Acid | 26.6 |
| Phenol Red | 10 | L-Threonine | 72 | L-Glutamic acid | 29.4 |
| Sodium Pyruvate | 110 | L-Tryptophan | 15 | L-Proline | 23 |
| L-Arginine HCl | 189 | L-Tyrosine 2Na $2H_2O$ | 54 | Nicotinamide | 1.5 |

TABLE 1-continued

| | SNU-1 (mg/l) | | SNU-1 (mg/l) | | SNU-1 (mg/l) |
|---|---|---|---|---|---|
| L-Cysteine 2HCl | 36 | L-Valine | 69 | Pyridoxine Hcl | 1.5 |
| L-Glutamine | 292 | D-Ca pantothenate | 1.5 | $NaHCO_3$ | 1000 |
| Glycine | 15 | Choline Chloride | 1.5 | | |
| L-Histidine HCl $H_2O$ | 63 | Folic Acid | 1.5 | | |

In the present invention, the fundamental medium is preferably supplemented with FGF-B (Fibroblast Growth Factor), ascorbic acid, EGF (Epidermal Growth Factor), hydrocortisone, IGF-1 (Insulin-like Growth Factor-1) or VEGF (Vascular Endothelial Growth Factor), and heparin and optionally with GA-1000 (Gentamycin Sulfate, Amphotericin-B) if needed.

More preferably, the fundamental medium is supplemented with fetal bovine serum (FBS) 20%, bFGF (Fibroblast Growth Factor) 1~40 ng/ml, ascorbic acid 0.1~5.0 µg/ml, EGF (Epidermal Growth Factor) 1~40 ng/ml, hydrocortisone 0.1~1 g/ml, IGF-I (Insulin-like Growth Factor-1) 1~40 ng/ml or VEGF (Vascular Endothelial Growth Factor) 1~5 ng/ml and heparin 20~25 µg/ml and optionally with GA-1000 (Gentamycin Sulfate, Amphotericin-B) if needed.

After being cultured for three days, the mononuclear cells which remain suspended are removed while only adherent cells are cultured. Among the mononuclear cells adherent to the vessel, only stem cells are proliferated. From 12 to 20 days after the isolation, rapid proliferation of the stem cells can be observed. In this context, the medium is preferably replaced with a fresh one every two or three days.

To obtain umbilical cord blood-derived pluripotent/multipotent stem cells from the culture, FACS using a flow cytometer with a sorting function (*Int. Immunol.*, 10(3):275, 1998), magnetic beads, or a panning method based on an antibody specific for mesenchymal stem cells (*J. Immunol.*, 141(8):2797, 1998) may be used. To obtain pluripotent/multipotent stem cells from a mass volume of culture, a column to which antibodies specific for molecules expressed on cell surfaces are immobilized (hereinafter referred to as "surface antigen") alone or in combination may be used.

Flow cytometry sorting may be performed by electrostatic droplet charging or cell capture. In either of the processes, an antibody specifically recognizing a surface antigen is fluorescence labeled after which the fluorescent intensity is measured from the labeled antibody-antigen conjugate and converted into electric signals to determine the expression level of the antigen of the cells. Further, different kinds of fluorophores may be used in combination to separate cells expressing different surface antigens. Among the fluorophores are FITC (fluorescein isothiocyanate), PE (phycoerythrin), APC (allo-phycocyanin), TR (TexasRed), Cy3, CyChrome, Red613, Red670, TRI-Color, and QuantumRed.

In FACS using a flow cytometer, the stem cells harvested from the culture by, for example, centrifugation may be immunostained directly with an antibody or may be proliferated in a suitable medium before immunostaining with an antibody. For the immunostaining, a target cell sample is mixed with a primary antibody specific for a surface antigen and incubated for 0.5 to 1 hour on ice. If the primary antibody is labeled with a fluorophore, the cell sample is washed and separated with a flow cytometer. If the primary antibody is not labeled with a fluorophore, the cell sample treated with the primary antibody is washed and mixed with a fluorescence-labeled secondary antibody that can bind to the primary antibody. Then, the immunostained cells are incubated again for 0.5 to 1 hour on ice and washed before being separated by a flow cytometer.

The umbilical cord blood-derived pluripotent/multipotent stem cells isolated according to the present invention have at least one of the following properties:

(a) showing a positive immunological characteristic to the transcription factors c-myc and ZNF281.

(b) adhering to a extracellular matrix-coated surface and forming cell colonies in a spindle or spherical shape 5 to 30 days after adhesion.

(c) showing a CPDL (cumulative population doubling level) of from 30 to 45.

(d) showing a negative immunological characteristic to CD14, CD31, CD34, CD45 and HLA-DR.

(e) ability to differentiate into mesodermal, endodermal and ectodermal cells.

(f) secreting at least one cytokine or chemokine selected from the group consisting of TIMP-2, TGF-β, RANTES CINC-3, EOTAXIN, GM-CSF, IFN-γ, IL-1b, IL-3, IL-6, IL-8, IL-10, IL12p40, IL13, IL-16, IP-10, Leptin, MCP-2, MIG, MIP-3a, b-NGFm, sTNFRI, and PFGF-bb.

The fact that the umbilical cord blood-derived pluripotent/multipotent stem cells of the present invention remain undifferentiated is evident from the expression of Oct-4, Sox-2, Rex-1, c-myc, and ZNF281 in the stem cells.

In addition, showing a CPDL (cumulative population doubling level) of from 30 to 45, the umbilical cord blood-derived pluripotent/multipotent stem cells of the present invention is highly proliferative. A karyotype analysis demonstrated that the cells of the present invention rapidly proliferate, but have a normal chromosomal structure.

The umbilical cord blood-derived pluripotent/multipotent stem cells of the present invention are immunologically negative to CD14, CD31, CD34, CD45 and HLA-DR, all known as hematopoietic stem cell markers or immunorejection-related markers. Due to the lack of such hematopoiesis- or immunorejection-related markers, the umbilical cord blood-derived stem cells of the present invention can be transplanted with minimal vascularization and immunorejection and thus can be effectively used in allogenic transplantation.

The umbilical cord blood-derived pluripotent/multipotent stem cells of the present invention also may differentiate into hepatocytes from the mesoderm and neurons and retina-related cells from the ectoderm as well as osteoblasts, chondrocytes and adipose cells from the mesoderm. Therefore, the umbilical cord blood-derived pluripotent/multipotent stem cells of the present invention can be used to treat a variety of diseases.

Further, the umbilical cord blood-derived pluripotent/multipotent stem cells of the present invention may secrete various cytokines or chemokines including TIMP-2, TGF-β, RANTES CINC-3, EOTAXIN, GM-CSF, IFN-γ, IL-1b, IL-3, IL-6, IL-8, IL-10, IL12p40, IL13, IL-16, IP-10, Leptin, MCP-2, MIG, MIP-3a, b-NGFm, sTNFRI, and PFGF-bb. Having the ability to secrete these cytokines or chemokines, the umbilical cord blood-derived pluripotent/multipotent stem cells of the present invention can be applied to the treatment of various diseases.

The novel nature of the umbilical cord blood-derived pluripotent/multipotent stem cells of the present invention comes from their having these characteristics.

As described above, the umbilical cord blood-derived pluripotent/multipotent stem cells of the present invention can be differentiated into various types of cells including osteoblasts, chondrocytes, adipose cells, hepatocytes and neurons, and thus find applications in therapies for various corresponding diseases. Therefore, the present invention provides a cell therapeutic agent comprising the umbilical cord blood-derived pluripotent/multipotent stem cells of the present invention or the cells differentiated therefrom. The cell therapeutic agent of the present invention can be applied to the treatment of various diseases including, for instance, neural diseases (e.g., degenerative neural diseases), osteoarthritis (e.g., degenerative arthritis, rheumatoid arthritis), bone loss (e.g., osteoporosis), hepatic diseases (e.g., hepato-cirrhosis), and cardiovascular diseases.

Preferably, the cell therapeutic agent of the present invention contains at least one diluent that can protect and maintain the cells. Buffered solutions such as physiological saline, PBS (Phosphate Buffered Saline), HBSS (Hank's balanced salt solution), and plasma or serum components may be used as the diluents.

In accordance with another aspect thereof, the present invention addresses a medium for culturing the novel stem cells. The medium is based on the EGM-2 or SNU-1 medium and supplemented with fetal bovine serum (FBS) 20%, bFGF (Fibroblast Growth Factor) 1~40 ng/ml, ascorbic acid 0.1~5.0 µg/ml, EGF (Epidermal Growth Factor) 1~40 ng/ml, hydrocortisone 0.1~1 µg/ml, IGF-I (Insulin-like Growth Factor-1) 1~40 ng/ml or VEGF (Vascular Endothelial Growth Factor) 1~5 ng/ml and heparin 20~25 µg/ml, and optionally with GA-1000 (Gentamycin Sulfate, Amphotericin-B) if needed.

The culturing medium for stem cells is novel and is used in the method for isolating umbilical cord blood-derived pluripotent/multipotent stem cells according to the present invention. Further, the culture medium of the present invention is useful for proliferating all adult stem cells including umbilical cord blood-derived stem cells and is applicable to the culturing of adult stem cells.

In accordance with a further aspect thereof, the present invention addresses a method for culturing stem cells comprising culturing and proliferating stem cells in the medium of the present invention. Preferably, the stem cells may be adult stem cells.

In one embodiment, the medium for culturing stem cells in accordance with the present invention may be used to culture the umbilical cord blood-derived pluripotent/multipotent stem cells of the present invention. While being cultured in the medium of the present invention, the umbilical cord blood-derived pluripotent/multipotent stem cells of the present invention may be preferably passaged 3~5 days after the formation of cell colonies in a spindle form. Cultivation is preferably performed in a 5% $CO_2$ condition and may be carried out for 5~30 days, but the present invention is not limited to these.

In accordance with still a further aspect thereof, the present invention addresses a method for increasing stemness of stem cells, characterized by a sphere culture or a three-dimensional culture of stem cells whereby stem cells are cultured. For the three-dimensional culture, MEF (Mouse embryonic fibroblast cell) is preferably used. Further, the stem cells may preferably be adult stem cells.

As used herein, the term "increasing stemness" means forming an embryonic stem cell-like colony or expressing transcription factors such as Oct4, Sox2, etc. at a higher level.

Advantageous Effects

When cultured in the presence of fibronectin, as explained in detail above, the human umbilical cord blood-derived pluripotent/multipotent stem cells of the present invention actively proliferate for a longer period of time without differentiating, compared to conventional adult stem cells. In addition, having the ability to differentiate to various kinds of cells such as chondrocytes, osteoblasts, and adipose cells, the pluripotent/multipotent stem cells of the present invention can be effectively applied to the treatment of conventionally incurable diseases, as well as neural diseases, cardiovascular diseases, and diseases of the skeletal system.

DESCRIPTION OF DRAWINGS

FIG. 1 is of photographs showing colonies formed after the mononuclear cells isolated from human umbilical cord blood were cultured for 14, 15, 16, 17 and 18 days (A, B, C, D and E, respectively) and cells after passage 3 (F);

FIG. 2 is a graph in which cumulative cell growth is plotted against time.

FIG. 3 shows karyotype analysis results after the umbilical cord blood-derived pluripotent/multipotent stem cells are cultured for a long period of time.

FIG. 4 is of flow cytograms showing the expression patterns of various markers on the umbilical cord blood-derived pluripotent/multipotent stem cells of the present invention.

FIG. 5 shows the expression patterns of various undifferentiation markers on the umbilical cord blood-derived pluripotent/multipotent stem cells of the present invention as measured by flow cytometry and immunostaining (A: flow cytogram of Oct4-expressing cells, B: image of immunostained Oct4 C: image of the nucleus stained in Oct4 expressed cells, D: overlapped image of Oct4 expression and nucleus staining).

FIG. 6 shows the expression of ZNF281 in terra-1, hUCB-MSC, AD-MSC and AM (upper panel) and in hUCB-MSC after 3~9 passages (lower panel) as analyzed by FACS.

FIG. 7 shows the expression of ZNF281, Oct4, Sox2, c-myc and Rex-1, all essential for the maintenance of undifferentiation, in the human umbilical cord blood-derived pluripotent/multipotent stem cells of the present invention, as measured by RT-PCR.

FIG. 8 is of photographs showing the differentiation of human umbilical cord blood-derived pluripotent/multipotent stem cells into osteoblasts, adipocytes, chondrocytes and neurons (A: non-osteogenic differentiation-induced control after staining with Alizarin Red S, B: osteogenic differentiation-induced cells after staining with Alizarin Red S, C: non-adipogenic differentiation-induced control after staining with Oil Red O, D: adipogenic differentiation-induced cells after staining with Oil Red O, E: chondrogenic differentiation-induced cells after staining with Toluidine Blue, F: pellet of chondrogenic differentiation-induced cells, G: cells immunostained with neural markers Tuj-1 and MAP2 after neural differentiation).

FIG. 9 shows RNA levels of the umbilical cord blood-derived pluripotent/multipotent stem cells after the induction of osteogenic differentiation and adipogenic differentiation, as measured by RT-PCR (PPAR-γ and FABP-4 are adipogenic differentiation markers and Collagen Type 1 is an osteogenic differentiation marker. PPAR-γ: Peroxisome Proliferator-Activated Receptor gamma, FABP-4: Fatty Acid Binding Protein-4, GAPDH: Glyceraldehyde-3-phosphate dehydrogenase).

FIG. 10 shows expression patterns of retina-related proteins in the umbilical cord blood-derived pluripotent/multipotent stem cells of the present invention.

FIG. 11 shows the secretion of various cytokines to culture media of the human umbilical cord blood-derived pluripotent/multipotent stem cells, as analyzed by an antibody array (A: hUCB-MSC1, B: hUCB-MSC2, C: hUCB-MSC3, D: an arrangement of antibodies, POS: Positive control, NEG: Negative control, GCSF: Granulocyte-Colony Stimulating Factor, GM-CSF: Granulocyte Monocyte-Colony Stimulating Factor, ICAM-1: Intra-Cellular Adhesion Molecule, IFN-γ: Interferon-γ, IL: Interleukin, MCP: Monocyte Chemoattractant Protein, M-CSF: Monocyte-Colony Stimulating Factor, MIG: Monokine induced by Interferon Gamma, MIP: Macrophage Inflammatory Protein, RANTES: Regulated upon Activation, Normal T-cell Expressed and Secreted, TGF-β: Transforming Growth Factor-β, TNF: Tumour Necrosis Factor, sTNFR: soluble Tumour Necrosis Factor Receptor, PDGF-BB: Platelet-Derived Growth Factor-BB, TIMP2: Tissue Inhibitor of Metalloproteinases-2).

FIG. 12 shows a three-dimensional culture of umbilical cord blood-derived pluripotent/multipotent stem cells by a monolayer and a sphere culture process. (A: a culture of umbilical cord blood-derived pluripotent/multipotent stem cells by a monolayer culture process and is the control for FIG. 12D. B: a three-dimensional culture of umbilical cord blood-derived pluripotent/multipotent stem cells by a sphere culture process in Example 11 at 100× magnification. C: a three-dimensional culture of umbilical cord blood-derived pluripotent/multipotent stem cells by a sphere culture process in Example 11 at 200× magnification. D: shows the expression patterns of the transcription factors Oct4 and Sox2 as measured by RT-PCR (Con: expression from cells maintained in a monolayer from FIG. 12A, Sphere: expression from cells maintained in a sphere culture.))

FIG. 13 shows a three-dimensional culture of umbilical cord blood-derived pluripotent/multipotent stem cells on STO cells (A and C: Image taken at 40× magnification, B: 100× magnification of FIG. 13A, D: 100× magnification of FIG. 13B).

MODE FOR INVENTION

A better understanding of the present invention may be obtained through the following examples which are set forth to illustrate, but are not to be construed as limiting the present invention.

Example 1: Culturing, Proliferation and Karyotype Analysis of the Umbilical Cord Blood-Derived Pluripotent/Multipotent Stem Cells Full term UCB samples (n=20) were collected immediately after delivery with the informed consent of the mothers. The full term UCB was mixed with HetaSep (Stem cells Technologies INC, Vancouver, BC) to deplete erythrocyte counts. Then, mononuclear cells were obtained by a typical Ficoll density gradient centrifugation. The mononuclear cells were seeded at a density of $1 \times 10^{5~8}$ cells/well on 6-well plates coated with 0.1 mg/ml-1 mg/ml fibronectin and maintained in SNU-1 or EGM-2 (Lonza) supplemented with EGM-2 SingleQuots containing 20% FBS. The EGM-2 SingQouts contained heparin, Ascorbic acid, rhEGF, hydrocortisone, VEGF, rhFGF-B, $R^3$-IGF-1, and GA-1000. The mononuclear cells which still remained non-adherent three days after culturing were removed while the medium was replaced with a fresh one every two or three days.

The adherent cells were observed to form colonies, exhibiting spindle-shaped morphology 5~30 days after being cultured under the condition of 5% $CO_2$ (FIG. 1A). Once formed, the colonies rapidly proliferated. The cells were suspended with 0.125% Trypsin-EDTA 3~7 days after the formation of colonies, and transferred to fresh dishes where the cells continued to be maintained (FIGS. 1B, 1C, 1D, 1E and 1F). FIG. 1 is of photographs showing the culture progress of the cells. As seen in FIG. 1, the cell colony grew larger with the lapse of time. In addition even after passage, the morphology of the cells stayed uniform (FIG. 1. isolation and proliferation of the umbilical cord blood-derived pluripotent/multipotent stem cells. Colonies formed after the mononuclear cells were cultured for 14 days (A), 15 days (B), 16 days (C), 17 days (D) and 18 days (E), and cells after passage 3 (F)).

While they continued to be cultured, the capacity of the isolated umbilical cord blood-derived pluripotent/multipotent stem cells to proliferate was analyzed by measuring CPDL (cumulative population doubling level) (Cristofalo et al., Proc. Natl. Acad. Sci., USA 95, 1998). Cells divide by binary fission. Hence, the growth rate of cells can be determined by the time which it takes for one cell to split into two, called the doubling time. A CDPL of 10 means 10 fissions of one cell, which results in the proliferation of one cell to approximately 1000 cells. One of the greatest problems of conventional umbilical cord blood-derived stem cells is that they have a significantly low proliferation capacity, compared to adipose tissue- or bone marrow-derived mesenchymal stem cells. Because clinical applications require a large number of stem cells, the proliferation capacity of stem cells is important. The measurement was performed as follows. First, umbilical cord blood-derived pluripotent/multipotent stem cells of three kinds were isolated from different samples of umbilical cord blood and were seeded at a density of $2 \times 10^5$ cells on 100 dishes and passaged at regular intervals of three to four days while being counted using a cytometer. Cell counting was performed until the cells stopped growing. CPDL values are obtained on the basis of the measurements of cell counts according to the following Math Formula 1

[Math Formula 1]

$$N_H/N_I = 2^X \text{ or } [\log(N_H) - \log(N_I)]/\log(2) = X$$

wherein, $N_I$ means the number of cells in the initial culture and $N_H$ means the number of cells in a saturation condition upon passage.

CPDL values were calculated while the cells continued to be maintained. For comparison, hUCB-EPC (human umbilical cord blood derived endothelial progenitor cells) was used as a control. The results are shown in FIG. 2. As can be seen in the graph of FIG. 2, hUCB-EPC had a CPDL of about 20 over two months whereas the CPDL of all the umbilical cord blood-derived pluripotent/multipotent stem cells from three different samples were observed to range between 40 and 45. These numerical values indicate that the cells can grow theoretically to the number of $10^{12}$ in one colony.

On the whole, cells with a capacity for great proliferation may be made to be cancerous, exhibiting explosive growth. Once cancerized, cells are likely to proliferate irrespective of various regulatory signals in the body, and thus cannot be used as a cell therapeutic agent and are inconsistent with the purpose of the study. Therefore, it must be determined whether the chromosomes of the umbilical cord blood-derived pluripotent/multipotent stem cells isolated according to the present invention are normal. In this context, a karyotype analysis was performed to examine the chromosomes of the cells. As can be seen in FIG. 3, the cells were found to have a normal chromosomal structure even after passage 10.

Example 2: Analysis of Surface Antigen of the Umbilical Cord Blood-Derived Pluripotent/Multipotent Stem Cells Flow cytometry was carried out to analyze the characteristics of the cells suspended in media. For phenotyping cell surface antigens, cells harvested after 3~4 passages were stained with a fluorescein isothiocyanate (FITC)- or phycoerythrin (PE)-conjugated antibody, and analyzed with FACSAria (Becton Dickinson, NY).

The surface antigens used to analyze the characteristics of the umbilical cord blood-derived pluripotent/multipotent stem cells (partially pluripotent/multipotent stem cell) isolated in the present invention included CD10 (T cell marker), CD14 (mononuclear cell marker), CD24 (epithelial cell marker), CD29 (mononuclear cell marker), CD31 (endothelial cell marker), CD34 (hematopoietic stem cell marker), CD44 (mesenchymal stem cell marker), CD45 (non-hematopoietic stem cell marker), CD51/61 (osteoclast marker), CD73 (mesenchymal stem cell marker), CD90 (mesenchymal stem cell marker), CD105 (mesenchymal stem cell marker), CD133 (hematopoietic stem cell marker), and HLA-DR (immunorejection-related marker), and were analyzed using a flow cytometer. The results are summarized in Table 2 and graphically depicted in FIG. 4.

TABLE 2

| CD Antigen on Umbilical Cord Blood-derived Pluripotent/multipotent Stem Cell | Positively stained cells/total cells (%) |
| --- | --- |
| CD10 | 0.2 ± 0.1 |
| CD14 | 2.0 ± 1.0 |
| CD24 | 68.7 ± 2.9 |
| CD29 | 100 ± 0.0 |
| CD31 | 0.4 ± 0.7 |
| CD34 | 3.5 ± 3.4 |
| CD44 | 100 ± 0.1 |
| CD45 | 0.0 ± 0.1 |
| CD51/61 | 6.4 ± 10.8 |
| CD73 | 99.6 ± 0.5 |
| CD90 | 99.7 ± 0.3 |
| CD105 | 99.5 ± 0.8 |
| CD133 | 0.1 ± 0.1 |
| HLA-DR | 2.0 ± 3.2 |

Example 3: Expression Pattern of ZNF281 and Core Transcription Factor in the Umbilical Cord Blood-Derived Pluripotent/Multipotent Stem Cells ZNF281 (Zinc finger protein 281) is one of the core transcription factors of ESC (Wang J et al. (2006) Nature 444, 364-368). ZNF281, also called ZBP-99, contains four Kruppel-type zinc fingers that collectively share 91% amino acid sequence similarity and 79% sequence identity with those found in ZBP-89. In addition, there are highly conserved amino acid sequences in the carboxy-terminal segments of the two genes. The predicted open reading frame of ZNF281 cDNA encodes a 99-kDa protein. EMSA (Electrophoretic mobility shift as say) showed that ZNF281 protein specifically binds to the GC-rich promoter elements of GASTRIN and ORNITHINE DECARBOXYLASE genes (Law D J et al. (1999) Biochem Biophys Res Commun 262, 113-120; Lisowsky T et a l. (1999) FEBS Lett 453, 369-

374). ZNF281 was identified as a c-MYC-associated protein by mass spectral multidimensional protein identification technology and tandem affinity purification (Koch H B et al. (2007) Cell Cycle 6, 205-217.).

Oct3/4 genes, such as POU family transcription factors, are known to not exist in differentiated tissues, but to be expressed particularly in undifferentiated stem cells which have a high proliferative capacity (Tai M-H. et al., Carcinogenesis 26:4 95, 2005; Tondreau T. et al., Stem cells, 23:1105, 2005). On the whole, Oct3/4 are therefore used as markers for embryonic stem cells and also as markers indicative of undifferentiation. The cell colonies were stained using Oct4 as a marker for sternness. As a result, many cells were found to have Oct4 stained around the nucleus. Flow cytometry also demonstrated the Oct4 expression in the cells.

To stain intracellular proteins, the cells were fixed at 4° C. overnight with 4% formaldehyde and permeabilized for 10 min with 0.1% Triton X-100 (Sigma-Aldrich). The slides and the dishes were incubated for one hour with an anti-human Oct4 mouse primary antibody (1:200), washed with PBS (phosphate buffered saline; Gibco), immunostained for one hour with an Alexa594-conjugated, goat anti-mouse IgG secondary antibody (Invitrogen) while the nucleus was countstained with DAPI.

As seen in FIGS. 5 and 6, many of the umbilical cord blood-derived pluripotent/multipotent stem cells were found to express Oct4 (FIG. 5A: flow cytogram of Oct4-expressing cells, B: image of immunostained Oct4 C: image of the nucleus stained in Oct4 expressed cells, D: overlapped image of Oct4 expression and nucleus staining).

Genes such as Oct4 are closely associated with the sternness of stem cells. In fact, attempts have recently been made to induce adult stem cells to have pluripotency similar to that of embryonic stem cells by getting them to overexpress genes such as Oct4, Sox2 and the like (Takahashi et al, Cell, 131(5), 861-872, 2007). Accordingly, the expression of these genes in stem cells is very important in keeping the stem cells at an undifferentiated state without losing sternness. Thus, to examine the expression patterns of ZNF281, Oct-4 and Sox2 in the umbilical cord blood-derived pluripotent/multipotent stem cells isolated according to the present invention, RT-PCR was performed.

For this, primers were constructed as in Table 3.

Example 4: Differentiation of the Umbilical Cord Blood-Derived Pluripotent/Multipotent Stem Cells into Osteoblasts The cells were induced to differentiate into osteoblasts. In this regard, the cells were allowed to adhere to culture dishes and incubated to about 70-80% confluency. Then, the culture medium was replaced with an osteogenic differentiation-inducing medium. The osteogenic differentiation-inducing medium was prepared by supplementing DMEM low glucose with 10% FBS plus 10 mM beta-glycerophosphate (Sigma-Aldrich), 0.1 µM D examethasone (Sigma-Aldrich), and 50 µM ascorbate (Sigma-Aldrich). The medium was replaced with a fresh one every third day while differentiation was induced for about two weeks.

After two weeks, the calcium mineralization attributed to the osteogenic differentiation was examined by Alizarin red S staining. The staining was conducted as follows. After the medium was removed, the cells were washed twice with distilled water and fixed at 4° C. for one hour in cold 70% EtOH. Then, the cells were washed again twice with distilled water and stained at room temperature for 10 min with 40 mM Alizarin red S, followed by washing five times with distilled water.

As seen in FIGS. 8A and 8B, in FIG. 8A no calcium was detected by Alizarin red S in the absence of differentiation whereas in FIG. 8B calcium appeared red when the cells were induced to differentiate into osteoblasts, which indicates that the umbilical cord blood-derived pluripotent/multipotent stem cells differentiated into osteoblasts releasing calcium.

Example 5: Differentiation of the Umbilical Cord Blood-Derived Pluripotent/Multipotent Stem Cells to Adipose Cells The cells were induced to differentiate into adipose cells. In this regard, the cells were allowed to adhere to culture dishes and cultured to about 70-80% confluency. Then, the medium was replaced with an adipocyte differentiation medium. The adipocyte differentiation medium was prepared by supplementing DMEM low glucose with 10% FBS plus 1 µM Dexamethasone, 10 µg/ml insulin (Sigma-Aldrich), 0.5 mM 3-isobutyl-1-methylxanthine (Sigma-Al-

TABLE 3

| Target Gene | Direction | Sequence | SEQ ID NO: |
|---|---|---|---|
| OCT-4 | sense primer | 5'-CGAAAGAGAAAGCGAACCAG-3' | 1 |
| | antisense primer | 5'-GCCGGTTACAGAACCACACT-3' | 2 |
| SOX2 | sense primer | 5'-CCTCCGGGACATGATCAG-3' | 3 |
| | antisense primer | 5'-TTCTCCCCCCTCCAGTTC-3' | 4 |
| C-MYC | sense primer | 5'-TACCCTCTCAACGACAGCAG-3' | 5 |
| | antisense primer | 5'-GGGCTGTGAGGAGGTTTG-3' | 6 |
| ZNF281 | sense primer | 5'-ACGTAACAGCGCAGACAGAA-3' | 7 |
| | antisense primer | 5'-GTGTTGAAGCCCAAGTGGTT-3' | 8 |
| REX-1 | sense primer | 5'-TGAAAGCCCACATCCTAACG-3' | 9 |
| | antisense primer | 5'-CAAGCTATCCTCCTGCTTTGG-3' | 10 |

As seen in FIG. 7, Oct-4, Sox2, c-myc, ZNF281, and REX-1 were expressed, indicating that the umbilical cord blood-derived stem cells of the present invention have pluripotency.

drich), and 0.2 mM indomethacin (Sigma-Aldrich). The differentiation medium was replaced with a fresh one every third day while differentiation was induced for about 2-3 weeks.

After 2~3 weeks, adipocyte differentiation was examined by Oil red O staining. For this, the medium was removed and the cells were washed in PBS and incubated at room temperature for 5 min in 10% formalin. The formalin was replaced with the same volume of a fresh one, followed by fixing the cells at room temperature for at least one hour. After removal of the formalin, the cells were washed with 60% isopropanol. The alcohol was completely evaporated before the cells were stained at room temperature for 10 min with Oil Red O. Immediately after this dye was removed, the cells were washed in distilled water.

Adipocytes appear red upon treatment with Oil red O because it stains lipid droplets red. As can be seen in FIGS. 8C and 8D, in FIG. 8C neither lipid droplets nor the red appearance was detected in the absence of adipocyte differentiation whereas in FIG. 8D when induced to differentiate into adipocytes, the cells were observed to have many lipid droplets and thus turn red).

Example 6: Differentiation of the Umbilical Cord Blood-Derived Pluripotent/Multipotent Stem Cells into Chondrocytes To induce the cells to differentiation chondrocytes, the cells were treated for three weeks with the rTGF-beta 3-containing chondrogenic differentiation medium (PT-3003) from Lonza, while the medium was replaced twice a week with a fresh one. Chondrogenesis was measured once a week.

To examine chondrogenic differentiation, toluidine blue staining was conducted. The cells were fixed for 10 hours with 4% formaldehyde and then for an additional 10 hours with picric acid. After cryosection, the cells were stained for 3 min with toluidine blue and counterstained for 3 sec staining with hematoxilin.

A pellet of chondrocytes does not collapse, but maintains a constant morphology and appears blue when stained with toluidine blue. As can be seen in FIGS. 8E and 8F, the cells subjected to chondrogenic differentiation were observed to be stained blue and maintain their morphology.

Example 7: Change in Gene Expression Level after Differentiation of the Umbilical Cord Blood-Derived Pluripotent/Multipotent Stem Cells into Osteoblasts and Adipocytes Stem cells were observed to significantly change in gene expression patterns while undergoing the differentiation process. As a rule, the expression level of PPAR-γ (Peroxisome Proloferator-activated Receptor-γ) or FABP4 (Fatty Acid Binding Protein 4) increases with the differentiation of stem cells into adipocytes while the expression level of Collagen Type 1 increases with the differentiation of stem cells into osteoblasts (Mat hews et al., J Am Acad Delivatol, 56(3), 472-492, 2007; Cho et al., J. Cell. Biochem., 96, 533-542, 2 005). Accordingly, after inducing differentiation, the expression level of a gene which is expressed in cells of a specific type indirectly indicates whether the stem cells have differentiated into the cells of the specific type. Experiments were conducted as follows.

Two to three weeks after differentiation into osteoblasts and adipocytes, total RNA was isolated from the cells using Trizol (Invitrogen). cDNA was synthesized using Accu-Power RT Premix (Bioneer), followed by PCR using Maxime PCRPreMix Kit (Intronbio).

For this, primers were designed as shown in Table 4, below.

TABLE 4

| Target Gene | Direction | Sequence | SEQ ID NO: |
|---|---|---|---|
| PPAR-γ | Sense primer | 5'-TGCTTTTGTAGGTACCTGGA-3' | 11 |
|  | Antisense primer | 5'-CATAAACTCTCGTGGAAGTG-3' | 12 |
| FABP4 | sense primer | 5'-GAGTCAACGGATTTGGTCGT-3' | 13 |
|  | Antisense primer | 5'-GACAAGCTTCCCGTTCTCAG-3' | 14 |
| Collagen Type 1 | Sense primer | 5'-GAGAGAGAGGCTTCCCTGGT-3' | 15 |
|  | Antisense primer | 5'-CACCACGATCACCACTCTTG-3' | 16 |

As is apparent from the data of FIG. 9, the expression levels of PPAR-γ and FABP4, which are markers for adipocyte differentiation, were greatly increased when the cells were induced to differentiate into adipocytes. Also, the expression level of collagen type 1, a maker for osteogenic differentiation, was greatly increased in cells going through differentiation. Meanwhile, the same level of the loading control GAPDH was detected in both cells which had and had not gone through differentiation, supporting the reasonability of the experiment.

Example 8: Differentiation of the Umbilical Cord Blood-Derived Pluripotent/Multipotent Stem Cells into Neurons The cells were induced to differentiate into neurons. First, the cells were pre-incubated for 24 hours in DMEM supplemented with 5% FBS and 10 ng/ml bFGF (basic Fibroblast Growth Factor). Thereafter, the cells were treated for 24 hours in DMEM containing 1% DMSO, 100 μM BHA, 0.5 mM VPA, 10 mM KCl, and 10 ng/ml NGF, and B27 to induce neural differentiation. To examine the neural differentiation, the cells were fixed with 4% paraformaldehyde and immunostained for the neural markers Tuj-1, MAP-2, GFAP, and Neurofilament-160. As a result, the four markers were observed to be expressed (FIG. 8G).

Example 9: Expression of Retina-Specific Proteins in Umbilical Cord Blood-Derived Mesenchymal Stem Cells The retina-related characteristics of the umbilical cord blood-derived pluripotent/multipotent stem cells were examined using immunofluorescence.

Expression patterns of retina-specific proteins in the cells were examined.

FIG. 10 is of photographs showing expression patterns of retina-specific proteins as measured by immunofluorescence. The expression patterns of PAX6 and Hu protein are shown in FIG. 10A. PAX6 is known as a retina progenitor marker and Hu protein is expressed specifically in gaglion cells and amacrine cells, which are constituents of the retina. They were not detected in a normal culture.

In FIG. 10B, opsin and rhodopsin are detected. Opsin is expressed specifically in cone cells while rhodpsin is specific for rod cells. In a no al culture, opsin was not detected, but expression of rhodopsin was observed.

Shown in FIG. 10C are the expression patterns of CRX and Recoverin. CRX is known as a pan-photoreceptor marker, and Recoverin as a photoreceptor marker. These markers were not detected in a normal culture (magnification×400, scale bar=50 μm).

Example 10: Analysis of Cytokines Released from the Umbilical Cord Blood-Derived Pluripotent/Multipotent Stem Cells The therapeutic capacity of stem cells is largely attributable to two effects: first, direct differentiation of stem cells into impaired cells; and secondly, the ability to secrete various cytokines or growth factors that induce positive alterations that lead to a therapeutic effect on pre-existing cells. Generally, stem cells are known to secrete various cytokines or growth factors, showing so-called paracrine effects (Kim et al. Cytokine. 2005). To examine the secretion patterns of the umbilical cord blood-derived pluripotent/multipotent stem cells isolated according to the present invention, a human Cytokine antibody array (RaybioTech. Norc ross, USA) was used.

Figure 11:
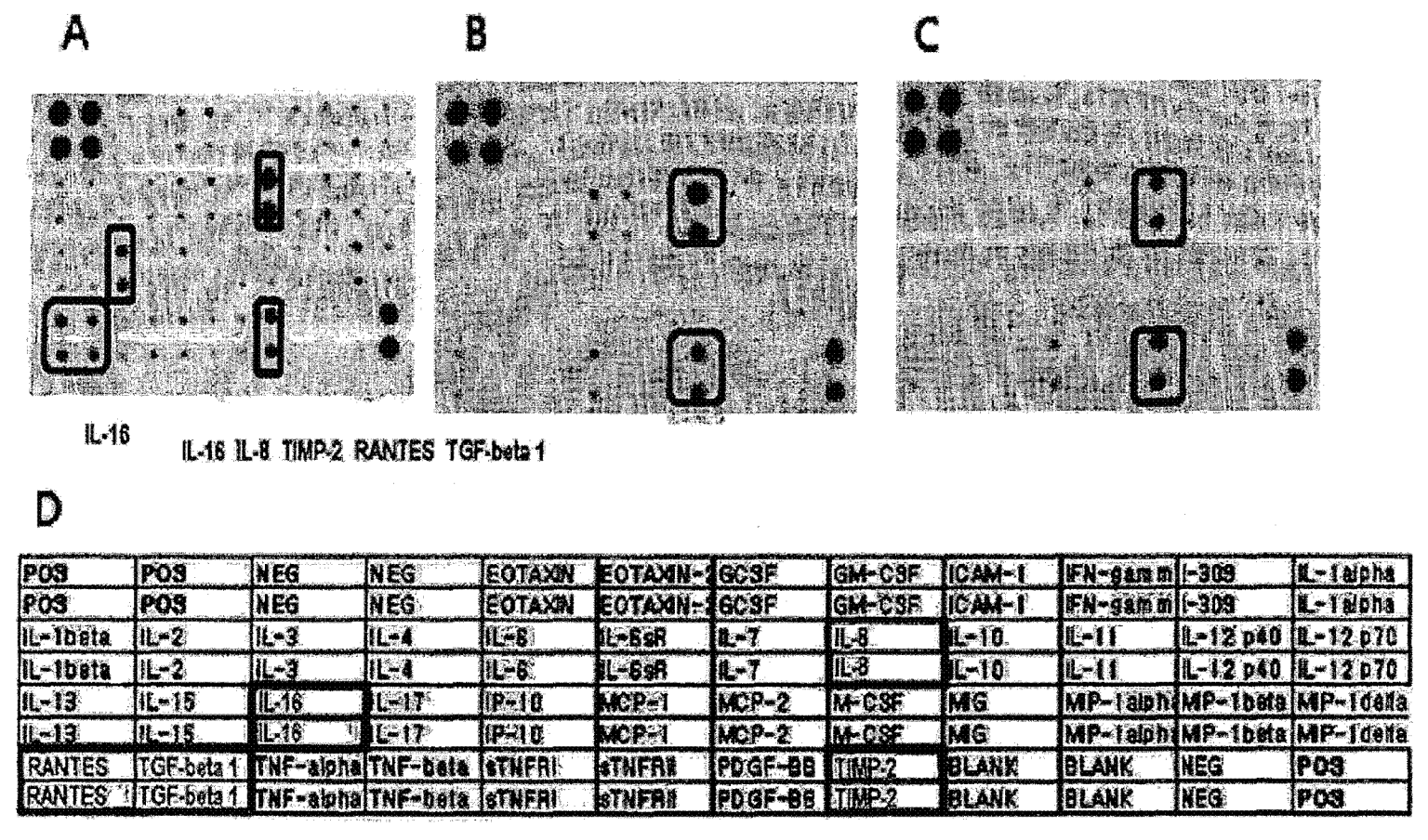

First, cells were stabilized for 24 hours in a medium free of both FBS and supplements, after which the medium was taken in an amount of 1 mL at regular 2 hour intervals. Each of the medium samples was collected in an amount of 100 μL to form a pool which was quantitatively analyzed for protein level, followed by assaying on an array As shown in FIG. 11, the umbilical cord blood-derived pluripotent/multipotent stem cells isolated from three different samples were all found to secrete IL-8 and TIMP-2. In addition, the secretion of various cytokines including TGF-β, RANTES, CINC-3, EOTAXIN, GM-CSF, IFN-γ, IL-1b, IL-3, IL-6, IL-10, IL12p40, IL13, IL-16, IP-10, Leptin, MCP-2, MIG, MIP-3a, b-NGFm, sTNFRI, and PFGF-bb was also observed (FIG. 11 shows array analysis results of hUCB-MSC1(A), hUCB-MSC2 (B) and hUCB-MSC3 (C) and an arrangement of antibodies (D)).

Example 11: 3-Dimensional Culture of the Umbilical Cord Blood-Derived Pluripotent/Multipotent Stem Cells Generally, adult stem cells grow, forming a monolayer in a culture dish. However, experiments demonstrated that the sternness of adults stem cells was increased when the adult stem cells were allowed to grow not in a 2-dimensional state, but as a sphere in a 3-dimensional state. In this regard, first, the culture dishes were coated with 0.7% agarose to a thickness of 5 mm or more so that the cells could not adhere to the bottom, but formed spheres. The cells were seeded at a density of less than 2000 cells/cm$^2$ to prevent adhesion between single cells. The spheres thus formed were separated from single cells using a 40 μm strainer. As can been seen in FIG. 12, the stem cells did not undergo cell death, but formed spheres, maintaining the characteristics of stem cells when they were cultured in a sphere culture system. As seen in FIGS. 12A-D, the expression levels of embryonic markers such as OCT4, SOX2 and the like in cells that were maintained in a sphere culture were observed to be higher compared to those which were maintained as a monolayer.

Embryonic stem cells are typically cultured on a layer of mouse embryonic fibroblast cells because the kemokines, such as LIF, from the mouse embryonic fibroblast cells play an important role in maintaining the morphology of ES cells and preventing the differentiation of ES cells. When cultured on a layer of mouse embryonic fibroblast cells, the umbilical cord blood-derived pluripotent/multipotent stem cells did not grow in a flat shape like typical adult stem cells, but formed 3-dimensional colonies. After their proliferation was suppressed by treatment with 0.1 mg/ml mitomycin C, STO cells were seeded at a density of 2×10$^5$ cells/ml on 0.1% gelatin-coated dishes and incubated for 24 hours, followed by seeding the umbilical cord blood-derived pluripotent/multipotent stem cells on the STO cell layer. As seen in FIG. 13, the cells were observed to proliferate on the STO cells in a pattern which was similar to that of embryonic stem cell with the lapse of time.

INDUSTRIAL APPLICABILITY

When cultured in the presence of fibronectin, the human umbilical cord blood-derived pluripotent/multipotent stem cells of the present invention actively proliferate for a longer period of time without differentiating, compared to conventional adult stem cells. In addition, having the ability to differentiate to various kinds of cells such as chondrocytes, osteoblasts, and adipose cells, the pluripotent/multipotent stem cells of the present invention can be effectively applied to the treatment of conventionally incurable diseases, as well as neural diseases, cardiovascular diseases, and diseases of the skeletal system.

The invention claimed is:

1. A method for isolating umbilical cord blood-derived pluripotent/multipotent stem cells expressing ZNF281 and a negative immunological characteristic to CD31 and CD45, comprising the steps of
 (a) culturing mononuclear cells isolated from umbilical cord blood in a culture vessel containing fibronectin,
 (b) removing non-adherent cells,
 (c) selecting for adherent cell colonies formed 5-30 days after culture, and
 (d) harvesting pluripotent/multipotent stem cells expressing ZNF281 and a negative immunological characteristic to CD31 and CD45, from the colonies, thereby providing highly proliferative umbilical cord blood-derived pluripotent/multipotent stem cells expressing ZNF281 and a negative immunological characteristic to CD31 and CD45,
 wherein the cells of (a), (c) and (d) are cultured in a SNU-1 medium supplemented with:
  fetal bovine serum (FBS);
  1-40 ng/ml Fibroblast Growth Factor (bFGF);
  0.1-5.0 µg/ml ascorbic acid;
  1-40 ng/ml Epidermal Growth Factor (EGF);
  0.1-1 ng/ml hydrocortisone;
  1-40 ng/ml Insulin-like Growth Factor-1 (IGF-1) or 1-5 ng/ml Vascular Endothelial Growth Factor (VEGF); and
  20-25 µg/ml heparin.

2. The method of claim 1, wherein the mononuclear cells are isolated by depleting erythrocytes in umbilical cord blood and thereafter using Ficoll-paque.

3. The method of claim 1, wherein the cells of (a), (c) and (d) are cultured in a form of spheres or three-dimensional structures in a culture medium.

4. The method of claim 3, wherein when the culture vessel is coated with fibronectin, said fibronectin is contained at a density of from 0.1 to 1 mg/mL.

5. The method of claim 1, wherein the fibronectin is derived from an animal.

6. The method of claim 5, wherein the animal is human.

7. The method of claim 1, wherein the fibronectin is a fragment or peptide sequence of fibronectin.

8. The method of claim 1, wherein the step (d) comprises utilizing an immunological property of stem cells to separate the stem cells.

* * * * *

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
cgaaagagaa agcgaaccag                                               20

<210> SEQ ID NO 2
<211> LENGTH: 20
```

```
<212> TYPE: DNA
<213> ORGANISM: Artificial Sequence
<220> FEATURE:
<223> OTHER INFORMATION: primer

<400> SEQUENCE: 2
gccggttaca gaaccacact                                           20

<210> SEQ ID NO 3
<211> LENGTH: 18
<212> TYPE: DNA
<213> ORGANISM: Artificial Sequence
<220> FEATURE:
<223> OTHER INFORMATION: primer

<400> SEQUENCE: 3
cctccgggac atgatcag                                             18

<210> SEQ ID NO 4
<211> LENGTH: 18
<212> TYPE: DNA
<213> ORGANISM: Artificial Sequence
<220> FEATURE:
<223> OTHER INFORMATION: primer

<400> SEQUENCE: 4
ttctcccccc tccagttc                                             18

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
taccctctca acgacagcag                                           20

<210> SEQ ID NO 6
<211> LENGTH: 18
<212> TYPE: DNA
<213> ORGANISM: Artificial Sequence
<220> FEATURE:
<223> OTHER INFORMATION: primer

<400> SEQUENCE: 6
gggctgtgag gaggtttg                                             18

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
acgtaacagc gcagacagaa                                           20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
```
gtgttgaagc ccaagtggtt                                                   20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
tgaaagccca catcctaacg                                                   20

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
caagctatcc tcctgctttg g                                                 21

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
tgcttttgta ggtacctgga                                                   20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
cataaactct cgtggaagtg                                                   20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
gagtcaacgg atttggtcgt                                                   20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
gacaagcttc ccgttctcag                                                   20

<210> SEQ ID NO 15
<211> LENGTH: 20
<212> TYPE: DNA
<213> ORGANISM: Artificial Sequence

```
<220> FEATURE:
<223> OTHER INFORMATION: primer

<400> SEQUENCE: 15
gagagagagg cttccctggt                                                    20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
caccacgatc accactcttg                                                    20
```